United States Patent [19]
Ghosh

[11] Patent Number: 5,597,898
[45] Date of Patent: Jan. 28, 1997

[54] NF-κB ACTIVATION REGULATORY PROTEIN, IκB-β

[75] Inventor: Sankar Ghosh, Madison, Conn.

[73] Assignee: Yale University, New Haven, Conn.

[21] Appl. No.: 388,756

[22] Filed: Feb. 15, 1995

Related U.S. Application Data

[60] Division of Ser. No. 71,819, Jun. 4, 1993, which is a continuation-in-part of Ser. No. 806,748, Dec. 13, 1991, abandoned, which is a division of Ser. No. 535,005, Jun. 7, 1990, Pat. No. 5,126,324.

[51] Int. Cl.$^6$ .................................................. C07K 14/47
[52] U.S. Cl. ............................................................. 530/350
[58] Field of Search .............................................. 530/350

[56] References Cited

PUBLICATIONS

Kerr, et al., The Rel–associated pp. 40 protein prevents DNA binding of Rel and NfκB: relationship with IκBβ and regulaton by phosphorylation; Genes & Development, 5:1464–1476, 1991.

Purified Human IκB Can Rapidly Dissociate the Complex of the NFκB Transcription Factor with its Cognate DNA Zabel and Baeuerle, Cell 61:255–265, Apr. 20, 1990.

Activation in vitro of NfκB by phosphorylation of its inhibitor IκB Ghosh and Baltimore, Nature, vol. 344:678–682, Apr. 1990.

Purified IκB–β Is Inactivated upon Dephosphorylation Link, et al., The Jrnl. of Bio. Chem., 267:239–246, Jan. 5, 1992.

Primary Examiner—Mindy Fleisher
Assistant Examiner—Terry A. McKelvey
Attorney, Agent, or Firm—Fish & Richardson P.C.

[57] ABSTRACT

The present invention provides a novel polypeptide, IκB-β, which binds to and affects NF-κB gene activation. Also provided is the nucleotide sequence encoding IκB-β and methods of identifying compositions which affect IκB-β\NF-κB complexes. Methods of treatment of disorders associated with NF-κB induced gene activation are also described herein.

1 Claim, 13 Drawing Sheets

Rabbit lung cytosol

↓ 0-40% ammonium sulfate
DEAE Sephacel gradient
CM-Sephadex
Sephacryl S-200 gel filtration NF-κB:IκB (α & β) complex
from Sephacryl-200 column

↓ 0.8% DOC

Dissociated NF-κB and IκB's

↓ Q-Sepharose anion exchange column

↙ ↘

NF-κB (p50:p65)      IκB-α and IκB-β mixture
(Flow through)      (~250-350 mM KCl)

FIG. 1A

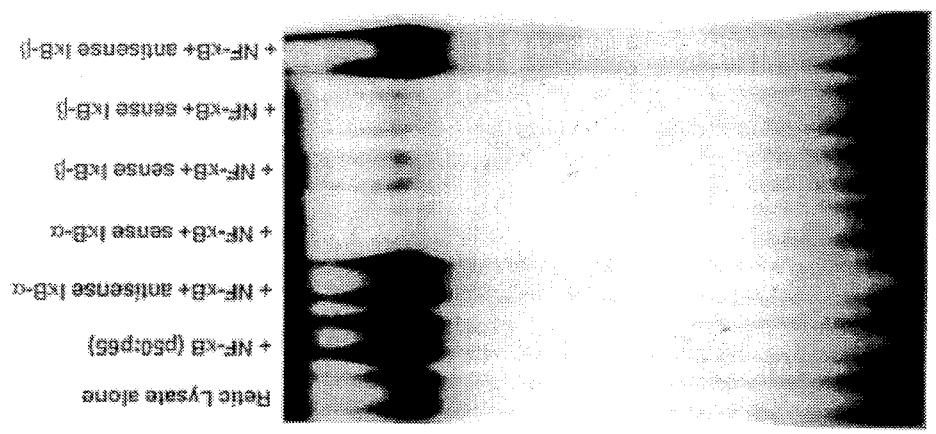
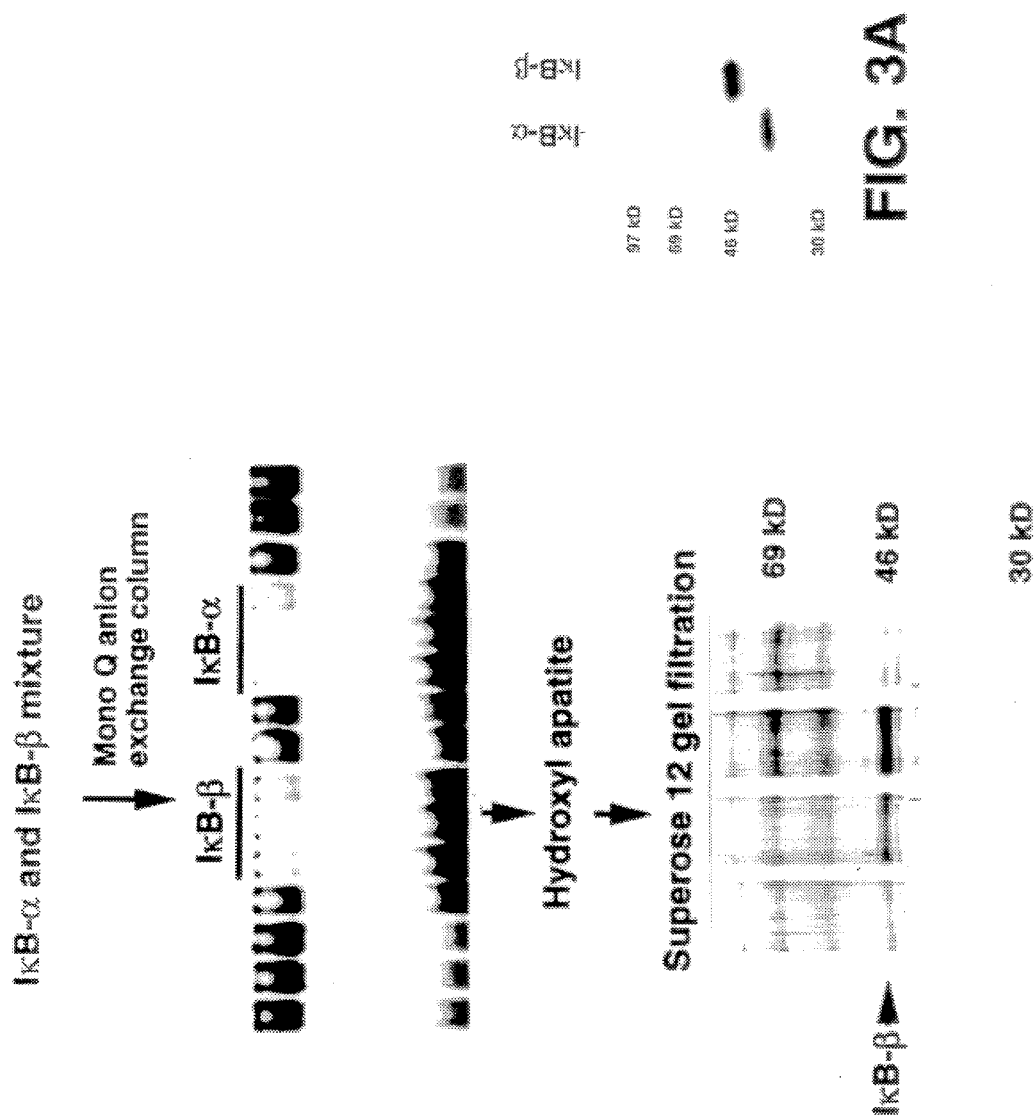

```
GCG CAC TGG AGC TCA TCG CAG AGC CCA GCG ACA GGC AGG CGA CCA CAG GGG    51
GCC ACC CGA GGT GGC TGG GGC CAT GGC CGG GGT CGC GTG CTT GGG GAA AAC   102
TGC GGA TGC CGA TGA ATG GTG CGA CAG CGG CCT GGG CTC TCT AGG TCC CGA   153
CGC AGC GGC TCC CGG AGG ACC AGG TCT GGG CGC AGA GCT TGG CCC AGA GCT   204
GTC GTG GGC GCC CTT AGT CTT TGG CTA CGT CAC TGA GGA TGG GAC ACA GC    255
CCT GCA CTT GGC TGT GAT TCA TCA GCA TGA GCC CTT CCT GGA TTT CCT CCT   306
GGG CTT TTC CGC CGG CCA CGA GTA CCT TGA CCT GCA GAA TGA CCT AGG CCA   357
AAC AGC CCT GCA TCT AGC AGC CAT CCT TGG GGA GGC ATC TAC AGT AGA GAA   408
GTT GTA TGC AGC CGG TGC AGG AGT GTT GGT GGC TGA GAG AGG GGG CCA CAC   459
GGC ATT GCA CTT GGC CTG CCG GGT CAG GGC ACA CAC GTG CGC GTG CGT ACT   510
GCT CCA GCC CCG TCC CAG CCA CCC AAG AGA TGC CTC AGA TAC CTA CCT CAC   561
TCA GAG CCA GGA CTG TAC CCC AGA CAC CAG CCA TGC CCC TGC TGC CGT GGA   612
TTC CCA ACC CAA CCC AGA GAA CGA AGA GGA GCC GCG TGA TGA AGA CTG GAG   663
GCT ACA ACT AGA AGC TGA AAA CTA TGA TGG CCA TAC CCC ACT CCA TGT AGC   714

TGT CAT CCA CAA AGA TGC AGA GAT GGT CCG GCT GCT CAG GGA TGC CGG AGC   765
CGA CCT CAA TAA ACC GGA GCC TAC GTG TGG CCG GAC CCC TCT GCA CCT GGC   816
AGT AGA AGC CCA GGC AGC CAG CGT GCT GGA ACT TCT CCT GAA AGC CGG TGC   867

TGA CCC CAC CGC CCG CAT GTA TGG GGG CCG CAC CCC GCT TGG CAG TGC CCT   918
GCT CCG GCC CAA CCC CAT CCT TGC CGG CCT CCT CCG TGC ACA TGG GGC CCC   969
TGA ACC TGA GGA CGG AGG AGA TAA GCT TAG CCC TTG CAG CAG CAG CGG CAG       1020
CGA CAG TGA CAG TGA CAA CAG AGA TGA GGG CGA TGA ATA TGA TGA CAT CGT       1071
GGC TCA CAG TGG CAG GAG CCT AAA CCG ACA ACC GCC TTC CCC GGC ATC AA        1122
ACC TCT TCC TGA TGA CCC CAA CCC TGC CTG ACT TAA GTG CTA ATA TTA ATA       1173
TAA TTT CCA ACT TAA TAA AAT TGC AGA CCT GAC AAC CAG AAA AAA AAA AAA       1224
AAA AAA AAA AAA AAA A                                                     1240
```

FIG. 2A

```
SEQ ID NO: 46)1  IVGGCVAHPHSWPWQVSLRTRFGKHFCGGTLISPEWVLTAAHCLKKSSRPS
SEQ ID NO: 48)2  :VGGCVAHPHSWPWQVSLRTRFG.HFCGGTLISPEWVLTAAHCL.KS:.RPS
SEQ ID NO: 47)3  VVGGCVAHPHSWPWQVSLRTRFGMHFCGGTLISPEWVLTAAHCLEKSPRPS
                 590^      600^      610^      620^      630^

1  SYKVILGAHQEVNLESHVQEIEVSRLFLEPTQADIALLKLSRPAVITDKVM
              2  SYKVILGAHQEVNLE:HVQEIEVSRLFLEPT:.DIALLKLS.PAVITDKV:
              3  SYKVILGAHQEVNLEPHVQEIEVSRLFLEPTRKDIALLKLSSPAVITDKVI
                 640^      650^      660^      670^      680^

1  PACLPSPDYMVTARTECYITGWGETQGTFGTGLLKEAQLLVIENEVCNHYK
              2  PACLPSP:Y:.V:.RTEC::ITGWGETQGTFG:.GLLKEAQL.VIEN.VCN:.Y.
              3  PACLPSPNYVVADRTECFITGWGETQGTFGAGLLKEAQLPVIENKVCNRYE
                 690^      700^      710^      720^      730^

1  Y-------ICAEHLARGTDSCQGDSGGPLVCFEKDKYILQGVTSWGLGC
              2  :CA.HLA.GTDSCQGDSGGPLVCFEKDKYILQGVTSWGLGC
              3  FLNGRVQSTELCAGHLAGGTDSCQGDSGGPLVCFEKDKYILQGVTSWGLGC
                 740^      750^      760^      770^      780^

1  ARPNKPGVYARVSRFVTWIEGMMRNNX
              2  ARPNKPGVY.RVSRFVTWIEG:MRNN
              3  ARPNKPGVYVRVSRFVTWIEGVMRNN
                 790^      800^      810^
```

FIG. 8

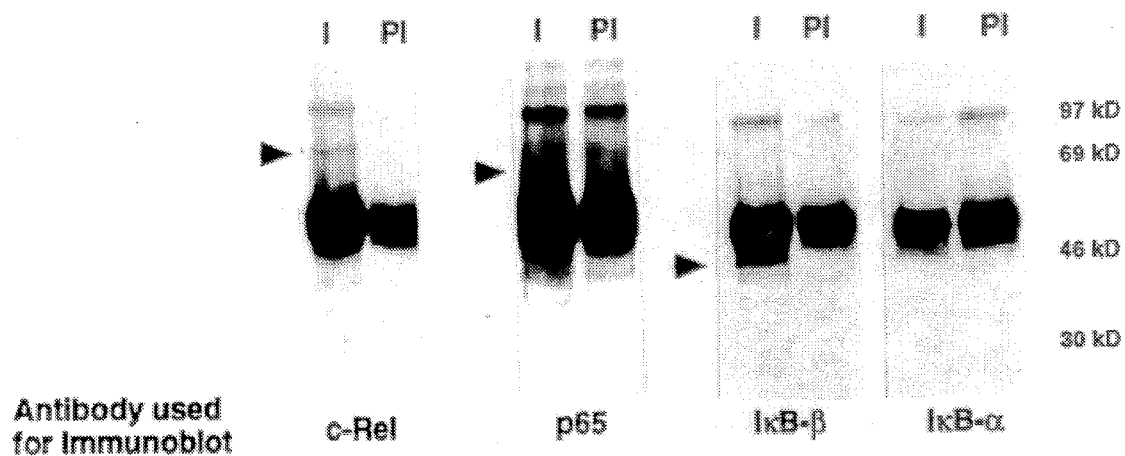
FIG. 6C
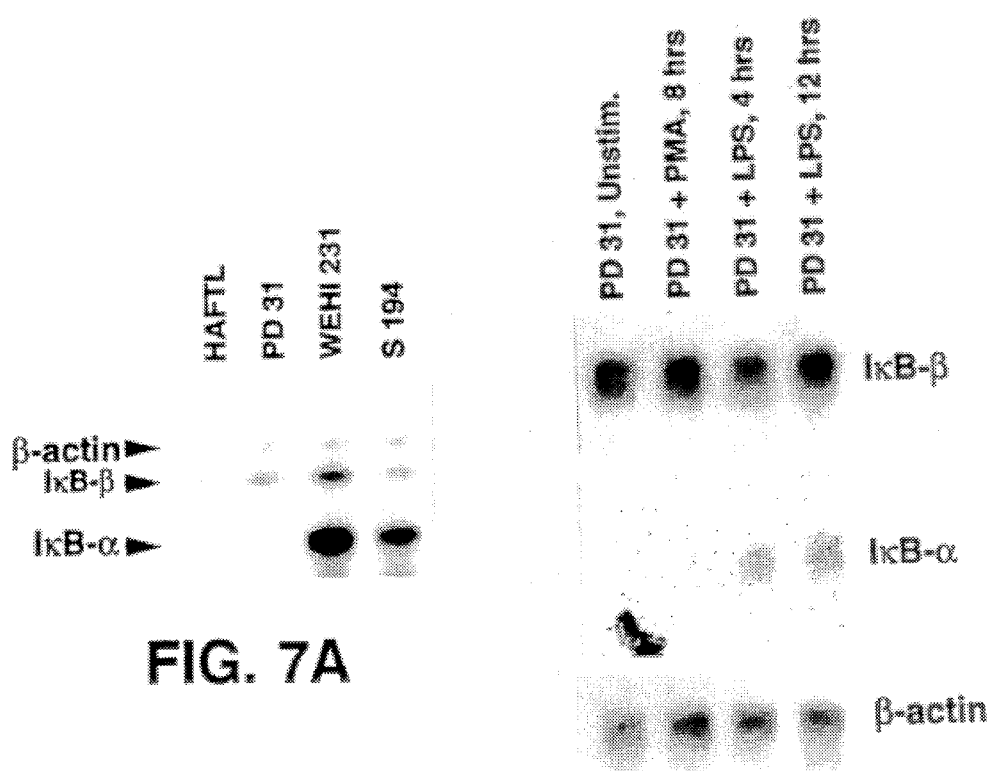
FIG. 7A
FIG. 7B

1

NF-κB ACTIVATION REGULATORY PROTEIN, IκB-β

The present invention was made with government support from grant no. RO1-AI 33443 from the National Institutes of Health. The government has certain rights in this invention.

This is a divisional of application(s) Ser. No. 08/071,819 filed on Jun. 4, 1993 which is a CIP of Ser. No. 07/806,748 filed Dec. 13, 1991, now abandoned, which is a DIV of Ser. No. 07/535,005 filed Jun. 7, 1990 now U.S. Pat. No. 5,126,324 which application(s) are incorporated herein by reference and to which application(s) priority is claimed under 35 USC§120.

BACKGROUND OF THE INVENTION

1. Field of the Invention

This invention relates generally to the field of regulation of gene expression and specifically to a novel protein, IκB-β, which contributes to the regulation of the transcription factor, NF-κB.

2. Description of Related Art

The nuclear factor-kappa B (NF-κB) is an inducible transcription factor which participates in the regulation of multiple cellular genes after treatment of cells with factors such as phorbol ester, lipopolysaccharide (LPS), interleukin-1 (IL-1) and tumor necrosis factor-α (TNF-α). These genes are involved in the immediate early processes of immune, acute phase, and inflammatory responses. NF-κB has also been implicated in the transcriptional activation of several viruses, most notably the type 1 human immunodeficiency virus (HIV-1) and cytomegalovirus (CMV) (Nabel, et al., *Nature*, 326:711, 1987; Kaufman, et al., *Mol. Cell. Biol.*, 7:3759, 1987; Sambucetti, et al., *EMBO J*, 8:4251, 1989).

NF-κB is a dimeric transcription factor that binds and regulates gene expression through decameric cis-acting κB DNA motifs. Although a p50/p65 heterodimer has traditionally been referred to as NF-κB and remains the prototypical and most abundant form, it has been recognized recently that several distinct but closely related homo- and heterodimeric factors are responsible for κB site-dependent DNA binding activity and regulation. The various dimeric factors are composed of members of the family of Rel-related polypeptides. One subclass of this family, distinguished by its proteolytic processing from precursor forms and lack of recognized activation domains, includes p50 (NFKB1) and p50B (NFKB2, p52), whereas the second subclass contains recognized activation domains and includes p65 (RelA), RelB, c-Rel, and the Drosophila protein Dorsal. All Rel-related members share a 300-amino acid region of homology, RHD, responsible for DNA binding and dimerization, called the Rel homology domain. In the cytoplasm, NF-κB and Rel proteins form a "Rel complex".

Activation of the NF-κB transcription factor and various related forms can be initiated by a variety of agents, including TNFα, phorbol 12-myristate 13-acetate (PMA), interleukin-1 (IL-1) and interleukin-2 (IL-2). Activation proceeds through a post-translational event in which preformed cytoplasmic NF-κB in the Rel complex is released from a cytoplasmic inhibitory protein. A common feature of the regulation of transcription factors which belong to the Rel-family is their sequestration in the cytoplasm as inactive complexes with a class of inhibitory molecules known as IκBs (Baeuerle and Baltimore, *Cell*, 53:211–217, 1988; Beg and Baldwin, *Genes Dev*. 7:2064–2070, 1993; Gilmore and Morin, *Trends in Genetics*, 9:427–433, 1993). Treatment of cells with different inducers, e.g., IL-1, TNF-α, LPS, dsRNA or PMA, results in dissociation of the cytoplasmic complexes and translocation of free NF-κB to the nucleus (Grilli, et al., *International Rev. of Cytology*, 143:1–62, 1993; Baeuerle and Henkel, *Annu. Rev. Immunol.*, 12:141–179, 1994). The dissociation of the cytoplasmic complexes is thought to be triggered by the phosphorylation and subsequent degradation of the IκB protein (Palombella, et al., *Cell*, 78:773–785, 1994; Ghosh and Baltimore, *Nature*, 344:678–682,1990). Transient IκB phosphorylation has been observed in several in vivo activation studies (Brown, et al., *Proc. Natl. Acad. Sci., U.S.A.*, 90:2532, 1993; Beg, et al., *Mol. Cell. Biol.*, 13:3301, 1993).

There are two major biochemically characterized forms of IκB proteins in mammalian cells, IκB-α and IκB-β (Ghosh and Baltimore, supra; Zabel and Baeuerle, *Cell*, 61:255–265, 1990). In addition, three other proteins have been cloned or implicated as IκBs: chicken pp40, the mammalian IκB-α homolog and inhibitor of the chicken oncogene, v-rel (Davis, et al., *Science*, 253:1268–1271, 1991; Stephens, et al., *Proc. Natl. Acad. Sci. USA*, 80:6229–6232, 1983); IκB-γ, a tissue specific form that arises from an alternative splice yielding the C-terminus of the p105 protein (Inoue, et al., *Cell* 68:1109–1120, 1992); and the candidate oncogene, Bcl-3 (Franzoao, et al., *Nature*, 359:339–342, 1992; Nolan, et al., *Mol. Cell Biol.*, 13:3557–3566, 1993; Ohno, et al., *Cell*, 60:991–997, 1990). A common feature of all of the cloned IκB proteins is the presence of multiple copies of a sequence motif known as ankyrin repeats (Beg and Baldwin, supra; Gilmore and Morin, supra).

However, while IκB-γ has been detected only in mouse pre-B cells (Ghosh, et al., 1990; Inoue, et al., supra), Bcl-3 can only be detected in very low amounts in some tissues. In addition, both IκB-γ (Liou, et al., *EMBO J.*, 11:3003–3009, 1992) and Bcl-3 (Franzoso, et al., supra; Naumann, et al., *EMBO J.*, 12:213–222, 1993; Nolan, et al., *Cell*, 64:961–969, 1991; Wulczyn, et al., *Nature*, 358:597–599, 1992) are specific for NFκB p50 dimers and only IκB-α and IκB-β interact with p65 and c-Rel, thus indicating that the responsibility for regulating the prototypical NF-κB activity is primarily carried out by these IκB isoforms.

IκB-α was cloned previously and its regulation has been studied quite extensively (Beg, et al., *Mol. Cell Bio.*, 13:3301–3310, 1993; Beg, et al., *Genes Dev.*, 6:1899–1913, 1992; Brown, et al., *Proc. Natl. Acad. Sci USA*, 90:2532–2536, 1993; Davis, et al., supra; Haskill, et al., *Cell*, 65:1281–1289, 1991; Henkel, et al., *Nature*, 365:82–85, 1993; Mellitis, et al., *Nucl. Acids Res.*, 21:5059–5066, 1993; Miyamoto, et al., *Mol. Cell Biol.*, 14:3276–3282, 1994; Palombella, et al., supra; Rice and Ernst, *EMBO J.*, 12:4685–4695, 1993; Scott, et al., *Genes Dev.*, 7:1266–1276, 1993; and Sun, et al., *Science*, 259:1912–1915, 1993). These studies indicated that IκB-α regulated NF-κB activity through a novel auto-regulatory feed-back loop. Signals that led to an induction of NF-κB activity resulted in the phosphorylation and rapid loss of IκB-α protein through proteolysis. However, the induced, nuclear NF-κB caused the subsequent upregulation of IκB-α mRNA levels due to the presence of NF-κB sites in the IκB-α promoter (de Martin, et al., *EMBO J.,*, 12:2773–2779, 1993; Le Bail, et al., *EMBO J.*, 12:5043–5049, 1993). The newly synthesized IκB-α mRNA was translated, and the accumulated IκB-α protein helped to shut down the NF-κB response, thus ensuring that responsive genes were activated only transiently. While this model explained some aspects of the regulation of NF-κB activity in cells, it failed to explain how some inducers, particularly bacterial lipopolysaccharide (LPS), could cause persistent long-term activation of NF-κB for as long as 36 hours. Persistent activation of NF-κB might also occur during differentiation, either in early embryonic development or in the development of B-cells or macrophages. Because a significant portion of the cytoplasmic Rel complexes are bound to IκB-β, it is possible that inducers like LPS or differentiation signals caused persistent NF-κB activation by affecting IκB-β complexes. However, the lack of a clone for IκB-β and reagents specific for the protein had prevented the determination of how and when complexes bound to IκB-β were activated.

Previous attempts to isolate and purify IκB-β have been unsuccessful. A study by Ghosh and Baltimore, supra, identified IκB activity as being associated with a 35 Kd protein in rabbit tissue. Zabel and Baeuerle (*Cell*, 61:255, 1990) then purified a complex which included p50:p65 and two forms of IκB, as determined by two distinct activities. While IκB-α was purified to homogeneity, IκB-β could only be partially purified based on a peak fraction of activity. A later study purported to purify a protein having IκB activity in the range of 40–43 KD and a pI of 4.8–5.0 (Link, et al., *J. Biol. Chem.*, 267:239, 1992). However, the fraction containing this activity was insufficient to allow reproducible peptide maps or amino terminal sequence analysis.

NF-κB gene regulation is involved in many pathological events including progression of acquired immune deficiency disease (AIDS), the acute phase response and the activation of immune and endothelial cells during toxic shock, allograft rejection, and radiation responses. In addition, NF-κB gene transactivation may be critical for HIV and CMV replication.

Therefore, identification of compositions which affect IκB-β/NF-κB complex integrity, and thus, affect NF-κB transactivation of genes, is critical for identification of specific inhibitors of complex dissociation, which would be effective as anti-inflammatory and immunosuppressive agents.

SUMMARY OF THE INVENTION

The present invention is bases on the discovery of a novel member of the IκB family of inhibitory molecules. This novel protein, IκB-β, binds to NFκB subunits p65 (RelA) and c-Rel and blocks NF-κB-DNA binding. While the IκB-α response is involved in response to transient situations of stress, the persistent response seen with IκB-β is typically involved in situations of chronic inflammation, infection, stress or differentiation.

In a first embodiment, the present invention provides an isolated IκB-β polypeptide having a molecular weight of 45 kD as determined by reducing SDS-PAGE. IκB-β polypeptide has a pI of about 4.6, binds to RelA and c-Rel, and has an amino acid sequence of SEQ ID NO: 2. Also included in the invention is an isolated polynucleotide sequence encoding IκB-β polypeptide.

In a second embodiment, the invention provides a method of identifying a composition which affects IκB-β/NF-κB complexes comprising incubating components comprising the composition, phosphorylated IκB-β, and NF-κB under conditions sufficient to allow the components to interact; and measuring the effect on the IκB-β/NF-κB complex caused by the composition. The method may optionally include NF-κB in a complex with IκB-β. Such compositions may include chymotrypsin inhibitors or anti-oxidants, for example.

In another embodiment, a method for identifying a composition which effects dissociation of IκB-β/NF-κB complexes comprising incubating components comprising the composition, an inducer of NF-κB, and an indicator cell and detecting NF-κB activity. The indicator cell utilized in the method of the invention preferably includes at least one copy of a κB binding motif operably linked to a reporter gene for detecting NF-κB activity.

The invention also provides a method of treating an immunological cell proliferative disorder associated with NF-κB induced gene activation in a subject comprising administering to the subject a therapeutically effective amount of an inhibitor of IκB-β/NF-κB complex dissociation.

BRIEF DESCRIPTION OF THE DRAWINGS

FIGS. 1A–1B, FIG. 1A shows purification scheme leading to a partially purified IκB (α and β) fraction (Ghosh and Baltimore, supra) which elutes from the Q-Sepharose column as a broad peak. FIG. 1B shows two IκB isoforms are resolved in the Mono Q column, where the peak that elutes earlier contains IκB-β. The purified fractions of IκB-β from the Superose 12 column were analyzed by silver staining.

FIGS. 2(A) AND 2B show the nucleotide sequence of the mouse IκB-β cDNA (SEQ ID NO: 1) and a schematic comparison between IκB-β and other members of the IκB family. FIG. 2(A) shows the sequence of the clone '15 f' along with the predicted 359 amino acid protein. The underlined sequence represents a putative casein kinase II site. The six ankyrin repeat sequences are indicated in boldface. The peptide sequences obtained from the purified rabbit protein corresponding to the predicted sequence from the cDNA are indicated. FIG. 2B shows schematic comparison between IκB-β and other members of the IκB family, mouse IκB-α, Bcl-3, IκB-γ and Drosophila cactus. The shaded boxes represent individual ankyrin repeats. The spacing between the third and fourth ankyrin repeats is similar to the arrangement in cactus and is not seen in the other proteins.

FIGS. 3A–3D show activity of IκB-β in vitro and expressed in vivo. FIG. 3A shows the cDNA's encoding the two IκBs which were cloned in a pCDNA 3 vector under the control of a T7 promoter and were used to program TNT rabbit reticulocyte coupled transcription-translation systems. The translated proteins were run on SDS-PAGE and visualized by fluorography. FIG. 3B shows that reticulocyte lysates contain an endogenous NF-κB that is primarily a p50:p65 heterodimer. Addition of purified rabbit p50:p65 NF-κB increases the signal, facilitating the subsequent assay for IκB activity. The TNT lysates were supplemented with purified rabbit NF-κB for the assays as indicated by '+NF-κB'. The two 'sense, β' lanes represent two translations programmed with 1 and 2 μg of plasmid respectively. The translation lysates were analyzed on a standard EMSA using an IgκB probe. FIG. 3C shows the GST-IκB fusion proteins purified on a glutathione-agarose affinity column, and purified proteins analyzed on SDS-PAGE using coomassie blue staining. FIG. 3D shows the specificity of GST-IκB proteins for p50, p65 and c-Rel. GST-IκB fusion proteins were partially purified by FPLC Mono Q and gel-filtration chromatography. An SDS-PAGE is shown.

FIGS. 4A–4B, FIG. 4A shows inhibition of DNA binding by transfected p50:p65 and p50:c-Rel in COS cells upon cotransfection with IκB-α and IκB-β. FIG. 4B shows inhibition of transcription as measured by inclusion of a luciferase reporter construct in transfections, similar to 3(A). T

FIG. 6A, 6B, and 6C show immunoblot and immunoprecipitation analyses of IκB-β. FIG. 6A shows different fractions from rabbit lung which are progressively purer chromatography fractions. The Superose 12 fraction is equivalent to the sample used for sequencing. The immunoblot with the mouse B-cell fractions was first used to examine IκB-β and then stripped and reprobed with an affinity purified IκB-β antibody. FIG. 6B shows immunoprecipitations carried out on $2 \times 10^7$ metabolically labeled Jurkat cells using the antiserum to IκB-β and the corresponding pre-immune serum. The bands that appear only with the immune serum are indicated. FIG. 6C shows immunoprecipitations carried out as in 6B on $1 \times 10^8$ unlabeled cells with proportionately greater amounts of immune and pre-immune serum. The immunoprecipitates were then fractionated on SDS-PAGE, electrophoretically transferred to PVDF membranes and immunoblotted with rabbit polyclonal antibodies to p65, c-Rel, IκB-α and IκB-β. FIGS. 7A–7B show expression of IκB-β and IκB-α in mouse B-cell lines, HAFTL (pro B), PD 31 (pre B), WEHI 231 (early mature B) and S 194 (plasma). FIG. 7B shows PD31 pre B cells stimulated with 2 μg/ml LPS for 4 hours, and 12 hours, and 25 ng/ml PMA for 8 hours. 20 μg or RNA was analyzed in each lane and the same blot was probed sequentially with IκB-β, β-actin and IκB-α.

FIG. 8B shows Jurkat cells stimulated with TNF-α (1 ng/ml) while 70Z/3 cells were treated with 25 ng/ml of PMA. FIG. 8C shows a schematic representation of the correlation between degradation of IκB-60 and IκB-β with the activation of NF-κβ, in cells treated with LPS or PMA.

DETAILED DESCRIPTION OF THE INVENTION

Figure 2B:
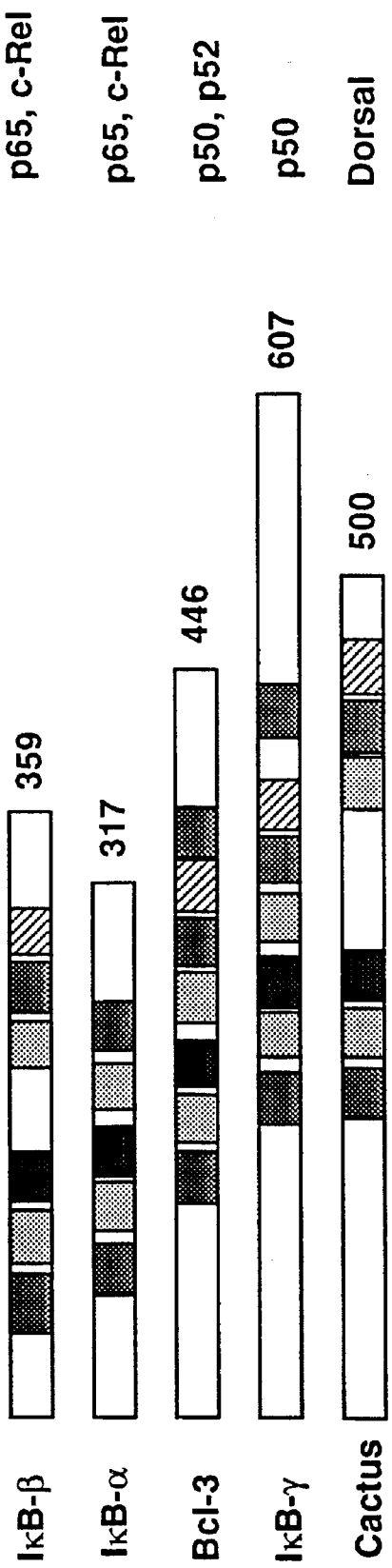

The NF-κB transcription factor complex is sequestered in the cytoplasm by IκB inhibitory proteins. Various cellular stimuli relieve this inhibition by mechanisms which are mostly unknown, leading to NF-κB nuclear localization and transactivation of its target genes. Thus, NF-κB and IκB proteins are involved in a tightly controlled mechanism of regulation. The present invention provides a novel IκB polypeptide, IκB-β, and polynucleotide sequences encoding the polypeptide.

In a first embodiment, the present invention provides an isolated IκB-β polypeptide consisting essentially of the amino acid sequence shown in FIG. 2(A) and SEQ ID NO:2. IκB-β polypeptide is characterized by having a molecular weight of 45 kD as determined by reducing SDS-PAGE; having a pI of about 4.6, binding to p65 (RelA) and c-Rel, and having an amino acid sequence of SEQ ID NO:2. The amino acid sequence of IκB-β polypeptide contains six consecutive ankyrin repeats, has an abundance of acidic amino acids, and contains a putative PEST domain.

The term "isolated" or "substantially pure" as used herein refers to IκB-β polypeptide which is substantially free of other proteins, lipids, carbohydrates or other materials with which it is naturally associated. One skilled in the art can purify IκB-β using standard techniques for protein purification. An illustration of a purification scheme for IκB-β is shown in FIG. 1A. The substantially pure polypeptide will yield a single major band on a non-reducing polyacrylamide gel. The purity of the IκB-β polypeptide can also be determined by amino-terminal amino acid sequence analysis.

The invention includes a functional polypeptide, IκB-β, and functional fragments thereof. As used herein, the term "functional polypeptide" refers to a polypeptide which possesses a biological function or activity which is identified through a defined functional assay and which is associated with a particular biologic, morphologic, or phenotypic alteration in the cell. Functional fragments of the IκB-β polypeptide, include fragments of IκB-β as long as the activity of IκB-β remains (e.g., binding to and inhibiting translocation of NF-κB to the nucleus). Smaller peptides containing the biological activity of IκB-β are included in the invention. Such peptides can be assayed for binding to NF-κB and/or inhibiting NF-κB transactivation of genes by methods commonly known to those of skill in the art, including methods described in the EXAMPLES herein. The biological function can vary from a polypeptide fragment as small as an epitope to which an antibody molecule can bind to a large polypeptide which is capable of participating in the characteristic induction or programming of phenotypic changes within a cell. A "functional polynucleotide" denotes a polynucleotide which encodes a functional polypeptide as described herein.

Minor modifications of the IκB-β primary amino acid sequence may result in proteins which have substantially equivalent activity as compared to the IκB-β polypeptide described herein. Such modifications may be deliberate, as by site-directed mutagenesis, or may be spontaneous. All of the polypeptides produced by these modifications are included herein as long as the activity of IκB-β is retained. Further, deletion of one or more amino acids can also result in a modification of the structure of the resultant molecule without significantly altering its activity. This can lead to the development of a smaller active molecule which would have broader utility. For example, it is possible to remove amino or carboxy terminal amino acids which may not be required for IκB-β activity.

The IκB-β polypeptide of the invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides an isolated polynucleotide sequence consisting essentially of a polynucleotide sequence encoding a polypeptide having the amino acid sequence of SEQ ID NO:2. The term "isolated" as used herein includes polynucleotides substantially free of other nucleic acids, proteins, lipids, carbohydrates or other materials with which they are naturally associated. Polynucleotide sequences of the invention include DNA, cDNA and RNA sequences which encode IκB-β. It is understood that all polynucleotides encoding all or a portion of IκB-β are also included herein, as long as they encode a polypeptide with IκB-β activity. Such polynucleotides include naturally occurring, synthetic, and intentionally manipulated polynucleotides. For example, IκB-β polynucleotide may be subjected to site-directed mutagenesis. The polynucleotide sequence for IκB-β also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of IκB-β polypeptide encoded by the nucleotide sequence is functionally unchanged e.g., binds NF-κB. In addition, the invention also includes a polynucleotide consisting essentially of a polynucleotide sequence encoding a polypeptide having an amino acid sequence of SEQ ID NO:2 and having at least one epitope for an antibody immunoreactive with IκB-β polypeptide.

The polynucleotide encoding IκB-β includes the nucleotide sequence in FIG. 2(A) (SEQ ID NO:1), as well as nucleic acid sequences complementary to that sequence. A complementary sequence may include an antisense nucleotide. When the sequence is RNA, the deoxynucleotides A, G, C, and T of FIG. 2(A) are replaced by ribonucleotides A, G, C, and U, respectively. Also included in the invention are fragments of the above-described nucleic acid sequences that are at least 15 bases in length, which is sufficient to permit the fragment to hybridize to DNA that encodes the protein of FIG. 2(A) (SEQ ID NO: 2) under stringent physiological conditions.

Specifically disclosed herein is a cDNA sequence for IκB-β which comprises a 1077 bp transcribed exon (SEQ ID NO: 1). The structure of the IκB-β mRNA is unique in that it contains very short 5' and 3' untranslated regions. In particular, the lack of any AUUUA sequences at the 3' end, unlike IκB-α mRNA, suggests that the IκB-β mRNA may be stable and not subject to rapid turnover.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences and 2) antibody screening of expression libraries to detect cloned DNA fragments with shared structural features.

Preferably the IκB-β polynucleotide of the invention is derived from a mammalian organism. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.,* 9:879, 1981).

The development of specific DNA sequences encoding IκB-β can also be obtained by: 1) isolation of double-stranded DNA sequences from the genomic DNA; 2) chemical manufacture of a DNA sequence to provide the necessary codons for the polypeptide of interest; 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA In addition, the DNA sequences of the invention can be obtained by synthesis using the polymerase chain reaction (PCR).

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as λgt11, can be screened indirectly for IκB-β peptides having at least one epitope, using antibodies specific for IκB-β. Such antibodies can be either polyclonally or monoclonally derived and used to detect expression product indicative of the presence of IκB-β cDNA.

A preferred method for obtaining DNA sequences encoding IκB-β is by the Polymerase Chain Reaction (PCR), which relies on an in vitro method of nucleic acid synthesis by which a particular segment of DNA is specifically replicated. Two oligonucleotide primers that flank the DNA fragment to be amplified are utilized in repeated cycles of heat denaturation of the DNA, annealing of the primers to their complementary sequences, and extension of the annealed primers with DNA polymerase. These primers hybridize to opposite strands of the target sequence and are oriented so that DNA synthesis by the polymerase proceeds across the region between the primers. Since the extension products themselves are also complementary to and capable of binding primers, successive cycles of amplification essentially double the amount of the target DNA synthesized in the previous cycle. The result is an exponential accumulation of the specific target fragment, approximately $2^n$, where n is the number of cycles of amplification performed (see, PCR Protocols, Eds. Innis, et al., Academic Press, Inc., 1990, incorporated herein by reference).

DNA sequences encoding IκB-β can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

Polynucleotide sequences encoding IκB-β can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Methods which are well known to those skilled in the art can be used to construct expression vectors containing the IκB-β coding sequence and appropriate transcriptional/translational control signals. These methods include in vitro recombinant DNA techniques, synthetic techniques, and in vivo recombination/genetic techniques. See, for example, the techniques described in Maniatis et al., 1989 Molecular Cloning A Laboratory Manual, Cold Spring Harbor Laboratory, New York.

A variety of host-expression vector systems may be utilized to express the IκB-β coding sequence. These include but are not limited to microorganisms such as bacteria transformed with recombinant bacteriophage DNA, plasmid DNA or cosmid DNA expression vectors containing the IκB-β coding sequence; yeast transformed with recombinant yeast expression vectors containing the IκB-β coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the IκB-β coding sequence; insect cell systems infected with recombinant virus expression vectors (e.g., baculovirus) containing the IκB-β coding sequence; or animal cell systems infected with recombinant virus expression vectors (e.g., retroviruses, adenovirus, vaccinia virus) containing the IκB-β coding sequence, or transformed animal cell systems engineered for stable expression. Since IκB-β has not been confirmed to contain carbohydrates, both bacterial expression systems as well as those that provide for translational and post-translational modifications may be used (e.g., mammalian, insect, yeast or plant expression systems).

Depending on the host/vector system utilized, any of a number of suitable transcription and translation elements, including constitutive and inducible promoters, transcription enhancer elements, transcription terminators, etc. may be used in the expression vector (see, e.g., Bitter et al., *Methods in Enzymology*, 153:516–544, 1987). For example, when cloning in bacterial systems, inducible promoters such as pL of bacteriophage λ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted IκB-β coding sequence.

In bacterial systems a number of expression vectors may be advantageously selected depending upon the use intended for the expressed. For example, when large quantities of IκB-β are to be produced, vectors which direct the expression of high levels of fusion protein products that are readily purified may be desirable. Those which are engineered to contain a cleavage site to aid in recovering are preferred. Such vectors include but are not limited to the *E. coli* expression vector pUR278 (Ruther et al., *EMBO J.*, 2:1791, 1983), in which the IκB-β coding sequence may be ligated into the vector in frame with the lac Z coding region so that a hybrid -lac Z protein is produced; pIN vectors (Inouye & Inouye, *Nucleic Acids Res.*, 13:3101–3109, 1985; Van Heeke & Schuster, *J. Biol. Chem.*, 264:5503–5509, 1989); and the like.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., Expression and Secretion Vectors for Yeast, in *Methods in Enzymology*, Eds., 1987; Wu & Grossman, 31987, Acad. Press, New York, Vol. 153, pp. 516–544; Glover, 1986, DNA Cloning, Vol. II, IRL Press, Washington, D.C., Ch. 3; and Bitter, 1987, Heterologous Gene Expression in Yeast, *Methods in Enzymology*, Eds. Berger & Kimmel, Acad. Press, New York, Vol. 152, pp. 673– 684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Washington, D.C.). Alternatively, vectors may be used which promote integration of foreign DNA sequences into the yeast chromosome.

In cases where plant expression vectors are used, the expression of the IκB-β coding sequence may be driven by any of a number of promoters. For example, viral promoters such as the 35S RNA and 19S RNA promoters of CaMV (Brisson et al., Nature, 310:511–514, 1984), or the coat protein promoter to TMV (Takamatsu et al., *EMBO J.*, 6:307–311, 1987) may be used; alternatively, plant promoters such as the small subunit of RUBISCO (Coruzzi et al., *EMBO J.*, 3:1671–1680, 1984; Broglie et al., *Science*, 224:838–843, 1984); or heat shock promoters, e.g., soybean hsp17.5-E or hsp17.3-B (Gurley et al., *Mol. Cell. Biol.*, 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, *Methods for Plant Molecular Biology*, Academic Press, N.Y., Section VIII, pp.421–463, 1988; and Grierson & Corey, *Plant Molecular Biology*, 2d Ed., Blackie, London, Ch. 7–9, 1988.

An alternative expression system which could be used to express is an insect system. In one such system, *Autographa californica* nuclear polyhedrosis virus (AcNPV) is used as a vector to express foreign genes. The virus grows in *Spodoptera frugiperda* cells. The IκB-β coding sequence may be cloned into non-essential regions (for example the polyhedrin gene) of the virus and placed under control of an AcNPV promoter (for example the polyhedrin promoter). Successful insertion of the IκBβ coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith, et al., *J. Viol.*, 46:584, 1983; Smith, U.S. Pat. No. 4,215,051).

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of IκB-β. Mammalian cell lines may be preferable. Such host cell lines may include but are not limited to CHO, VERO, BHK, HeLa, COS, MDCK, −293, and WI38.

Mammalian cell systems which utilize recombinant viruses or viral elements to direct expression may be engineered. For example, when using adenovirus expression vectors, the IκB-β coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the protein in infected hosts (e.g., see, Logan & Shenk, *Proc. Natl. Acad. Sci. USA*, 81:3655–3659, 1984). Alternatively, the vaccinia virus 7.5K promoter may be used. (e.g., see, Mackett, et al., *Proc. Natl. Acad. Sci. USA*, 79:7415–7419, 1982; Mackett, et al., *J. Virol.*, 49:857–864 1982; Panicali, et al., *Proc. Natl. Acad. Sci. USA*, 79:4927–4931, 1982). Of particular interest are vectors based on bovine papilloma virus which have the ability to replicate as extrachromosomal elements (Sarver, et al., *Mol. Cell. Biol.*, 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the IκB-β gene in host cells (Cone & Mulligan, *Proc. Natl. Acad. Sci. USA*, 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the IκB-β cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell*, 11:223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22:817, 1981) genes can be employed in tk$^-$, hgprt$^-$ or aprt$^-$ cells respectively. Also, antimetabolite resistance can be used as the basis of selection for dhfr, which confers resistance to methotrexate (Wigler, et al., *Natl. Acad. Sci. USA*, 77:3567, 1980; O'Hare, et al., *Proc. Natl. Acad. Sci. USA*, 78:1527, 1981); gpt, which confers resistance to mycophenolic acid (Mulligan & Berg, *Proc. Natl. Acad. Sci. USA*, 78:2072, 1982; neo, which confers resistance to the aminoglycoside G-418 (Colberre-Garapin, et al., *J. Mol. Biol.*, 150:1, 1981); and hygro, which confers resistance to hygromycin (Santerre, et al., *Gene*, 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA*, 85:8047, 1988); and ODC (ornithine decarboxylase) which confers resistance to the ornithine decarboxylase inhibitor, 2-(difluoromethyl)-DL -ornithine, DFMO (McConlogue L., *In: Current Communications in Molecular Biology*, Cold Spring Harbor Laboratory ed., 1988).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the IκB-β of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive (e.g., which bind) with IκB-β polypeptide or immunoreactive fragments of IκB-β. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature,* 256:495, 1975). The term antibody as used in this invention is meant to include intact molecules as well as fragments thereof, such as Fab and F(ab')$_2$, which are capable of binding an epitopic determinant on IκB-β.

The term "antibody" as used in this invention intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual,* Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the IκB-β polypeptide of the invention can be prepared using an intact polypeptide or fragments containing small peptides of interest as the immunizing antigen. The polypeptide, such as SEQ ID NO:2, or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., mouse, rat, goat, rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *current Protocols in Immunology,* Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, in the present invention, an anti-idiotype antibody produced from an antibody which binds to the IκB-β polypeptide of the invention can bind to the site on p65 or c-Rel to which IκB-β binds, thereby preventing IκB-β from binding to and sequestering NF-κB in the cytoplasm.

In another embodiment, the invention provides a method for identifying a composition which affects the integrity of IκB-β\NF-κB complexes. While not wishing to be bound to a particular theory, the effect may be inhibiting or stimulating a protease, for example, which degrades phosphorylated IκB-β. Such compositions may be effective as anti-inflammatory and immunosuppressive drugs. The method comprises incubating components, which include the composition to be tested, IκB-β, preferably as phosphorylated IκB-β, and NFκB, for a time and under conditions sufficient to allow the components to interact, then subsequently measuring the effect, e.g., on degradation of IκB-β, the composition has on the IκB-β\NF-κB complex. For example, the observed effect may be inhibition or stimulation of IκB-β degradation. For example, a composition which inhibits a protease will prevent the protease from degrading IκB-β, thereby prohibiting NF-κB from being translocated to nucleus and inhibiting transactivation of genes by NF-κB. The effect the composition has on the stability of IκB-β can be determined by various methodologies including immunological, nucleic acid and protein analyses. The IκB-β can be labeled so that its fate can be determined. Examples of labels include a radioisotope, a fluorescent compound, a bioluminescent compound, a chemiluminescent compound, a metal chelator or an enzyme. Those of ordinary skill in the art will be able to ascertain such, using routine experimentation.

The method of the invention for identifying a composition which affects IκB-βNF-κB complexes includes NF-κB, preferably bound to or complexed with IκB-β. A composition which affects IκB-β\NF-κB complexes may include a chymotrypsin inhibitor, such as TPCK. A composition may also include an anti-oxidant, such as PDTC. A candidate cytoplasmic protease which can degrade IκB-β following stimulation is a ubiquitous 700 kD multisubunit proteosome which has chymotrypsin-like activity (Vinitsky, et al., *Biochemistry,* 31:9421, 1992). A proteosome as described herein is a multicatalytic enzyme complex.

The invention also includes a method of identifying a composition which affects IκB-β\NF-κB complexes comprising incubating components including the composition to be tested, an inducer of NF-κB and an indicator cell, and detecting NF-κB activity. The inducer of NF-κB can be added prior to or following the addition of the composition to be tested. Preferably, it is added after the composition is added. Typically, the inducer of NF-κB is selected based on the ability to affect IκB-β/NF-κB complexes. Inducers of NF-κB include cytokines such as IL-1, and lipopolysaccharide (LPS). Other inducers will be known to those of skill in art. Typically, a preferred composition identified by the method of the invention will inhibit dissociation of an IκB-β/NF-κB complex.

The method of the invention is performed in an indicator cell. An "indicator cell" is one in which activation of NF-κB can be detected. Examples of mammalian host indicator cells include the pre-B cell line, 70Z/3, Jurkat T, COS, BHK, 293, CHO, HepG2, and HeLa cells. Other cell lines can be utilized as indicator cells, as long as the level of NF-κB can be detected. The cells can be recombinantly modified to contain an expression vector which encodes one or more additional copies of the κB binding motif, preferably operatively linked to a reporter gene. The cells can also be modified to express IκB-β and NF-κB. Preferably, the expression vector which encodes NF-κB, contains the coding region for the p65 or c-Rel subunit of NF-κB, to which IκB-β binds.

The host cell may be a yeast modified by recombinant DNA to express NF-κB, a protease gene derived from a cDNA expression library and κB motiflinked to a reporter gene. The expression of the protease would result in IκB degradation and activation of NF-κB, hence induction of reporter activity. In the presence of the composition, the protease would be inhibited resulting in no reporter activity. Examples of markers typically used in yeast reporter studies include β galactosidase (β-gal), HIS3 and LEU2 nutrient selection markers.

The reporter gene is a phenotypically identifiable marker for detection of stimulation or inhibition of NF-κB activation. Markers preferably used in the present invention include the LUC gene whose expression is detectable by a luciferase assay. Examples of markers typically used in prokaryotic expression vectors include antibiotic resistance genes for ampicillin (β-lactamases), tetracycline and chloramphenicol (chloramphenicol acetyl-transferase). Examples of such markers typically used in mammalian expression vectors, which are preferable for the present invention, include the gene for adenosine deaminase (ADA), aminoglycoside phosphotransferase (neo, G418), dihydrofolate reductase (DHFR), hygromycin-B-phosphotransferase (HPH), thymidine kinase (TK), xanthine guanine phosphoribosyltransferse (XGPRT,gpt) and β-galactosidase (β-gal).

Transformation of a host cell with recombinant DNA may be carried out by conventional techniques which are well known to those skilled in the art. Where the host is prokaryotic, such as E. coli, competent cells which are capable of DNA uptake can be prepared from cells harvested after exponential growth phase and subsequently treated by the CaCl$_2$ method by procedures well known in the art. Alternatively, MgCl$_2$ or RbCl can be used. Transformation can also be performed after forming a protoplast of the host cell or by electroporation.

When the host is a eukaryote, which is preferable in the method of the invention, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982).

In the present invention, κB binding motif polynucleotide sequences, preferably operatively linked to a reporter gene, IκB-β and NF-κB polynucleotide sequences may be inserted into recombinant expression vectors. The term "recombinant expression vector" refers to a plasmid, virus or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication and a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedron promoters).

Detection of NF-κB activity in the method of the invention can be detected by measuring the level of the gene product of the reporter gene. Methods of detection may be immunological, by nucleic acid analysis, by protein analysis, by nutrient selection, or by enzymatic assay, for example. Other common methods will be known to those of skill in the art.

In another embodiment, the invention provides a method of treating an immunopathological disorder associated with NF-κB gene activation in a subject. Preferably, the immunopathological disorder is associated with IL-1 production or LPS stimulation. The method comprises administering to the subject a therapeutically effective amount of an inhibitor of IκB-β\NF-κB complex dissociation. The term "immunopathological disorder" refers to any disease which involves the immune response or immunity in general. "Therapeutically effective" as used herein, refers to that amount of inhibitor that is of sufficient quantity to ameliorate the cause of the NF-κB disorder. "Ameliorate" refers to a lessening of the detrimental effect of the disorder in the patient receiving the therapy. The subject of the invention is preferably a human, however, it can be envisioned that any animal with a NF-κB disorder can be treated by the method of the invention, for example, a SCID mouse grafted with human bone marrow (humanized SCID). Examples of immunopathological disorders which can be treated by the method of the invention include acquired immunodeficiency disorder (AIDS), toxic shock syndrome, chronic inflammation (e.g., arthritis), allograft rejection, ultraviolet and radiation responses, and disorders associated with the activation of T cells, B cells and macrophages during the immune response and the acute phase response and disorders associated with advanced cancer such as tumor necrosis factor-mediated cachexia. Essentially, any disorder which is etiologically linked to NF-κB\IκB-β association/dissociation would be considered susceptible to treatment.

Specifically, the method of the invention may be used to treat a subject having sepsis or one or more of the symptoms of sepsis. The method comprises administering to a subject displaying symptoms of sepsis or at risk for developing sepsis, a therapeutically effective amount of an inhibitor of dissociation IκB-β\NF-κB complexes. An inhibitor may be identified by a method of the invention as described herein. Such symptoms which may be ameliorated include those associated with a transient increase in the blood level of TNF, such as fever, hypotension, neutropenia, leukopenia, thrombocytopenia, disseminated intravascular coagulation, adult respiratory distress syndrome, shock and multiple organ failure. Patients who require such treatment include those at risk for or those suffering from toxemia, such as endotoxemia resulting from a gram-negative bacterial infection, venom poisoning, or hepatic failure, for example. In addition, patients having a gram-positive bacterial, viral or fungal infection may display symptoms of sepsis and may benefit from such a therapeutic method as described herein. Those patients who are more particularly able to benefit from the method of the invention are those suffering from infection by *E. coli, Haemophilus influenza* B, *Neisseria meningitides*, staphylococci, or pneumococci. Patients at risk for sepsis include those suffering from burns, gunshot wounds, renal or hepatic failure.

In another embodiment, the invention includes a method of modulating the activation of a virus associated with NF-κB transactivation comprising contacting a virus-containing cell with a modulating effective amount of an inhibitor of IκB-β\NF-κB complex dissociation. The term "modulate" refers to either inhibiting or stimulating the activation of a virus. Any virus which is transactivated by NF-κB is included, for example, human immunodeficiency virus (HIV) or herpes viruses such as cytomegalovirus (CMV). The method of modulating activation of CMV is useful, for example, in treating CMV retinitis.

When an inhibitor of NF-κB\IκB-β dissociation is administered to a subject, the inhibitor can be administered parenterally by injection or by gradual infusion over time. The inhibitor can be administered intravenously, intraperitoneally, intramuscularly, subcutaneously, intracavity, transdermally, or extracorporeally. Methods for delivery of the inhibitor also include orally, by encapsulation in microspheres or proteinoids, by aerosol delivery to the lungs, or transdermally by iontophoresis or transdermal electroporation. Other methods of administration will be known to those skilled in the art.

Preparations for parenteral administration of an inhibitor of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In yet another embodiment, the present invention provides a method of treating a cell proliferative disorder in a subject, wherein the disorder is associated with NF-κB\IκB-β complex association/dissociation. Such a disorder may be for example, due to persistant activation of NF-κB. The term "cell-proliferative disorder" denotes malignant as well as non-malignant cell populations which morphologically often appear to differ from the surrounding tissue. For example, the method may be useful in treating malignancies of the various organ systems, such as, for example, lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine, and cancer of the esophagus.

The method is also useful in treating non-malignant or immunological-related cell-proliferative diseases such as psoriasis, pemphigus vulgaris, Behcet's syndrome, acute respiratory distress syndrome (ARDS), ischemic heart disease, post-dialysis syndrome, leukemia, rheumatoid arthritis, acquired immune deficiency syndrome, vasculitis, lipid histiocytosis, septic shock and inflammation in general. Essentially, any disorder which is etiologically linked to IκB-β\NF-κB complexes would be considered susceptible to treatment.

Due to the high level of expression of IκB-β in the testes, there are a variety of applications using the polypeptide, polynucleotide, and antibodies of the invention related to this tissue. Such applications include treatment of cell proliferative disorders associated with NF-κB gene activation in the testes. Various testicular developmental or acquired disorders can also be subject to IκB-β applications. These disorders may include, but are not limited to viral infection (e.g., viral orchitis), autoimmunity, sperm production or dysfunction, trauma, and testicular tumors.

The foregoing is meant to illustrate, but not to limit, the scope of the invention. Indeed, those of ordinary skill in the art can readily envision and produce further embodiments, based on the teachings herein, without undue experimentation.

EXAMPLE 1

MATERIALS and METHODS

1. Purification of IκB-β from rabbit lungs

The purification of IκB-β was carried out from a total of 4 kgs of rabbit lungs, with 4 individual purifications of 1 kg each. The initial steps in the purification were as reported in Ghosh, S. and Baltimore, D. *Nature*, 344:678–682, 1990, for the purification of IκB-α. The present purification differed from that carried out previously as the phenyl sepharose step was eliminated and an FPLC hydroxyl apatite column (Pentax) was used instead of the conventional resin. The partially purified NF-$_\kappa$B:IκB complex was dissociated with 0.8% DOC and then fractionated on a Q-sepharose anion-exchange column. The majority of NF-$_\kappa$B activity eluted in the 100 mM KCl flow-through, while the IκBs remained bound to the column. The bound proteins were eluted with a gradient from 100–600 mM KCl, when the IκB's eluted as a broad peak between 250–350 mM KCl. The mixture of IκBs were then fractionated on a FPLC Mono Q column with gradient from 100–800 mM KCl. The IκB activity eluted in two peaks and the peak eluting earlier (at –300 mM KCl) contained IκB-β. The pool of IκB-β was further chromatographed on a hydroxyl apatite and an FPLC Superose-12 gel filtration column. 50 μl of the peak fractions containing IκB-β activity were analyzed on SDS-PAGE and the proteins were visualized by silver staining. The yield of the pure protein after the final Superose-12 gel filtration column was approximately 2 μg, of which about 1.8 μg was used for SDS-PAGE and electro-blotting to nitrocellulose membrane. Following transfer approximately 1 μg protein (–20 pmol) was available for digestion with trypsin and sequencing.

2. Sequencing the purified IκB-β protein

The 45 kD protein band on nitrocellulose was digested with trypsin, releasing peptides that were separated by narrow-bore HPLC as described previously (Ghosh, et al., *Cell* 62:1019–1029, 1990). Six peaks were observed over the trypsin autolytic background. Using previously described microanalysis techniques (Erdjument-Bromage, et al., *RX Angeletti* ed., 4:419–426, 1993), sequence information was obtained from 4 peptides, one of which was a mixture. The sequence of the three pure peptides were T15, L-YAAxA(G)VCVAE (SEQ ID NO:3) with 1.4 picomole yield, T27, LQLEAENYDGxTPLxVA(v) (SEQ ID NO:4) at 1.6 pmol and T41, PLHLAVEAQAAD(V)LELL (SEQ ID NO:5) at 1.5 pmol. Sequences are in the one letter annotation known to those of skill in the art; x indicates that no residue could be identified at this position, parentheses indicate identifications with lower degree of confidence and amino acids in lower case parenthesis were present at very low levels only.

3. Cloning IκB-β cDNA from mouse LyD9 pro-B cell cDNA library

Degenerate PCR primers, containing EcoRI and Bam HI restriction sites, were synthesized using sequences from the peptides T27 (SEQ ID NO:4) and T41 (SEQ ID NO:5) in both orientations. Rabbit lung total RNA was used to synthesize the cDNA template for PCR, using random hexamers for priming. Approximately 1/10th of the reverse transcribed reaction mixtures were used for the PCR reactions with different combinations of the primers; 5' T27+3' T41 and 5' T41 and 3' T27. The PCR products synthesized after 35 cycles of amplification did not contain any obvious product upon ethidium bromide staining. Therefor the entire reaction mix was purified and digested with the two unique restriction enzymes and then ligated into a Bluescript vector digested with the same enzymes. A few clones were obtained from both ligations, and miniprep DNA isolated from them were sequenced. One of the clones from the 5' T27+3' T41 contained a 160 bp insert that had sequences that could encode the peptides used to design the primers. On Northern blots this insert, when used as a probe, hybridized to a single band of 1.3 kb from both rabbit lung and mouse LyD9 RNA. This result strongly suggested that there was only a single species of mRNA in mouse that was homologous to the 160 bp PCR product from rabbit. Therefore, this insert was used as a probe to screen different libraries, either from commercial sources or made from mouse LyD9 or 22D6 cell lines. No clones were obtained from multiple screenings of multiple libraries that were all size selected for larger cDNA's (>1kb), and therefore, a new cDNA library in λ gtl1, with cDNA from the mouse pro-B cell line, LyD9. The cDNA was size selected from 0.7 to 1.6 kb to increase the proportion of mRNA's encoding IκB-β, that has a size of 1.3 kb. Upon screening $10^6$ clones from this library, 15 positive clones were obtained which all contained the same cDNA. Clone 15f was selected for subsequent analysis.

4. In vitro translations

In vitro translations of both IκB-α and IκB-β were carried out in rabbit reticulocyte lysates that were obtained from Promega. The transcription/translation coupled systems (TnT) were used with either T7 or T3 RNA polymerases depending on the particular construct. After a 90 min incubation, 2 μl of the lysates were analyzed on a SDS-PAGE and the synthesized proteins detected by fluorography.

5. Expression of GST-IκB fusions

Fusions of IκB-α and IκB-β with glutathione-S-transferase were generated by PCR assisted cloning into the GEX-2t vector. The constructs in DH-5α cells were grown overnight in small cultures. The overnight cultures were diluted 1:50 in media and grown to a density of about 0.3 $OD_{600}$ when they were induced with 0.4 mM IPTG for 4 hours. The cells were then harvested and lysed by freeze-thawing followed by sonication. The soluble extract was used to purify the GST-fusion proteins. When using IκB-β as antigen, the extract was first purified by glutathione-agarose affinity chromatography followed by FPLC Mono Q anion exchange and Sephacryl gel-filtration chromatography.

6. Immunoprecipitation analysis

Cells ($2\times10^7$) were labeled with Translabel (ICN) for 45 minutes in RPMI containing 5% dialyzed fetal calf serum. Following labeling, cells were lysed in 1.2 mls of TNT buffer (20 mM Tris-HCl, 1% Triton X-100 and 200 mM NaCl), centrifuged and the supernatant collected. 300 μl of the supernatant was used for each immunoprecipitation and the volume was made up to 1 ml with TNT buffer. Then 5 μl of the preimmune or immune serum and 20 μl of a 1:1 slurry of protein A sepharose was added and incubated overnight at 4° C. The samples were then centrifuged and the protein A sepharose washed 5 times with TNT buffer and finally the pellet was boiled for 5 minutes in 2×SDS sample buffer and loaded onto SDS-PAGE. Following electrophoresis the gels were fixed and incubated in Amplify (Amersham). The dried gels were then exposed for fluorography.

7. Western blot analysis

Western blot analysis was generally carried out using approximately 25 μg of cellular extracts. Proteins were electroblotted from SDS-polyacrylamide gels onto PVDF membrane. The membrane was blocked with 5% Blotto and the primary antibody was added in Blotto. Subsequent washes and incubation with the secondary antibody were done in TTBS. Proteins detected by the primary antibody were visualized by carrying out a chemiluminescence assay using reagents from Amersham (ECL) and exposure to film. The IκB-β antibodies used were either affinity purified rabbit polyclonal antibody raised against a peptide (Santa Cruz Biotechnology) or affinity purified antibody against the recombinant full-length protein. The p50 and IκB-β antibodies were rabbit polyclonal antisera raised against purified, recombinant proteins.

8. Northern blot and ribonuclease protection assays

Northern blot analysis was carried out on either total RNA or poly A+RNA according to standard protocols. RNA samples (25 μg for total, 3 μg for poly A+) were fractionated on formaldehyde-agarose gels. Transfer of RNA to nylon membranes were carried out using the Stratagene Posiblot apparatus and nucleic acids were UV cross-linked to the membranes. The DNA probes for hybridization were labeled by a random priming protocol and hybridized in 50% formamide buffers at 42° C. Following hybridization the blots were washed under increasingly stringent conditions with the final wash typically done with 0.2×SSC, 0.5% SDS at 65° C.

Ribonuclease protection assays were carried out according to protocols and reagents from Ambion (RPA II kit). Antisense probes of 250, 200 and 150 bases for β-actin, IκB-β and IκB-α were made by in vitro transcription using T7 RNA polymerase. The labeled probes were excised from a polyacrylamide gel and eluted. The probes were then hybridized overnight to 10 μg of total RNA for each sample at 42° C. The samples were then digested with RNAse and analyzed by gel electrophoresis.

9. Transfection by DEAE-dextran protocol

Approximately $10^7$ cells were used for each transfection. The DNA was taken up in $MgCl_2/CaCl_2$ containing buffer.

Then DEAE-dextran was added to 0.5 µg/ml final concentration in a total volume of 1 ml. The cells were taken up in this solution and incubated for 20 minutes. Then media with chloroquine was added and incubated for a further 30 minutes. The cells were spun down, washed and then plated in fresh media for 48 hours. Finally, the cells were harvested, washed with PBS lysed in a NP-40 containing buffer and the extract assayed for luciferase activity according to protocols from Promega.

10. NP-40 lysis procedure for subcellular fractionation

Approximately $2 \times 10^7$ cells were used for each time point. The cells were pelleted by low speed centrifugation, washed with PBS and then resuspended in 200 µl of buffer A (20 mM Hepes, pH 7.9, 10 mM NaCl, 1 mM EDTA, 1 mM DTT and protease inhibitors). After allowing the cells to swell, 5 µl of 0.5% NP-40 was added and gently vortexed for 10 seconds. Following centrifugation the pelleted nuclei were washed with Buffer A, resuspended in 50 µl of Buffer C (20 mM Hepes, pH 7.9, 0.4 M NaCl, 1 mM EDTA, 1 mM DTT and protease inhibitors) and shaken for 15 minutes at 4° C. The extract was centrifuged and to the supernatant glycerol was added to 5%. The cytoplasmic fraction obtained after the low speed centrifugation was centrifuged at 100,000 g for 1 hour and the supernatant was adjusted to 100 mM NaCl and 5% glycerol.

EXAMPLE 2

PURIFICATION AND SEQUENCING OF IκB-β FROM RABBIT LUNGS

The purification of IκB-β was carried out from rabbit lung cytosolic extracts that were previously demonstrated to contain significant quantities of NF-κB:IκB complexes (Ghosh and Baltimore, supra; Ghosh, et al., supra). The purification takes advantage of the difference in chromatographic properties between the NF-κB:IκB complexes and free IκB proteins. The initial steps of the purification protocol led to a partially purified NF-κB:IκB (α and β) complex which was then dissociated with deoxycholate (DOC) and separated into NF-κB and IκB pools using anion exchange chromatography (Ghosh and Baltimore, supra). The mixture of IκB-α and IκB-β isoforms was subjected to additional chromatographic steps (e.g., Mono Qanion exchange, hydroxylapatite, Superose 12) that yielded a highly enriched fraction of IκB-β. These steps had not been utilized previously in prior art attempts to purify IκB-β. The purified protein was fractionated on a SDS-polyacrylamide gel and transferred to nitrocellulose membrane. The protein on the membrane was stained with Ponceau S and the deeply staining IκB-β band was excised. The protein was digested on the membrane with trypsin and the eluted peptides were fractionated on a reverse phase HPLC column. Four peptides were sequenced, one of which was a mixture while the other three were pure peptides.

FIGS. 1A–1B show purification of IκB-β from rabbit lung cytosol. FIG. 1A shows the purification scheme leading to a partially purified IκB (α and β) fraction (Ghosh and Baltimore, supra) which elutes from the Q-Sepharose column as a broad peak. FIG. 1B shows the two IκB isoforms are resolved in the Mono Q column, where the peak that elutes earlier contains IκB-β. The purified fractions of IκB-β from the Superose 12 column were analyzed by silver staining.

EXAMPLE 3

MOLECULAR CLONING AND SEQUENCING OF IκB-β cDNA

The sequence of two of the peptides identified in EXAMPLE 2 revealed that they were derived from ankyrin repeats. Degenerate PCR primers based on these ankyrin related peptide sequences were synthesized and used for PCR on cDNA from rabbit lung RNA as template. A 160 bp fragment was obtained upon cloning the products of the PCR, that when sequenced was found to contain the complete sequence necessary to encode the peptides used to generate the primers. The entire fragment encoded nearly two ankyrin repeats. Northern blot analysis indicated that this 160 bp fragment was derived from a 1.3 kb mRNA that was present in rabbit lungs, as well as the mouse B cell line LyD9. The 160 bp fragment was used as a probe to screen a 0.7–1.6 kb size fractioned library of mouse LyD9 cDNA and multiple clones were obtained. The sequence of these clones revealed an open reading frame of 359 amino acids that can encode a protein with a predicted molecular weight of 41 kD which is smaller than the 45 kD size of the partially purified protein fraction. The predicted pI of 4.6, however, is in close agreement with that of the purported partially purified protein (Link, et al., *J. Biol. Chem.*, 267:239–246, 1992). The cDNA sequence includes the entire 160 bp sequence of the PCR fragment and also contains the third peptide sequence that had not been used for cloning and thus the cloned cDNA most likely encodes the Iκ-β protein that was purified.

FIGS. 2(A) and 2B show the nucleotide sequence of the mouse IκB-β cDNA (SEQ ID NO:1) and a schematic comparison between IκB-β and other members of the IκB family. FIG. 2(A) shows the sequence of the clone '15f' along with the predicted 359 amino acid protein is presented. The underlined sequence represents a putative casein kinase II site. The six ankyrin repeat sequences are indicated in boldface. The peptide sequences obtained from the purified rabbit protein corresponding to the predicted sequence from the cDNA are indicated. FIG. 2(B) shows a schematic comparison between IκB-β and other members of the IκB family, mouse IκB-α, Bcl-3, IκB-γ and Drosophila cactus. The shaded boxes represent individual ankyrin repeats. The spacing between the third and fourth ankyrin repeats is similar to the arrangement in cactus and is not seen in the other proteins.

The primary sequence indicates that IκB-β contains six consecutive ankyrin repeats, an organization that is a hallmark of all cloned IκB proteins (FIG. 2B) (Beg and Baldwin, *Mol. Cell. Biol.*, 7:2064–2070, 1993; Gilmore and Morin, *Trends in Genetics*, 9:427–433, 1993). Comparing the sequence of IκB-β with the other IκB proteins reveals that the similarity between ankyrin repeats at the same position in different IκBs is greater than between repeats in the same IκB (Gilmore and Morin, supra). The greater spacing between the third and fourth ankyrin repeats in IκB-β is similar to the arrangement in cactus, the IκB-like inhibitor of the Drosophila rel-homolog dorsal, and is not seen in the other IκB proteins (Geisler, et al., *Cell*, 71:613–621, 1992; Kidd, S., *Cell*, 71623–635, 1992). The carboxy terminal region is rich in the proline, glutamic acid and serine residues which suggests that it may be a PEST domain, sequences that have been implicated to signal rapid protein turnover (Haskill, et al., *Cell*, 65:1281–1289, 1991). Although Iκ-β contains the same number of serine/threonine residues as IκB-α, including a putative casein kinase II site, it lacks the protein kinase C phosphorylation site present in the other isoform (Haskill, et al., supra). The structure of the IκB-β mRNA is unique in that it contains very short 5' and 3' untranslated regions. In particular, the lack of any AUUUA sequences at the 3' end, unlike IκB-α mRNA, suggests that the IκB-β mRNA may be stable and not subject to rapid turnover (Caput, et al., *Proc. Natl. Acad. Sci. USA*, 83:1670–1674, 1986; Davis et al., *Science,* 253:1268–1271, 1991; Haskill, et al., supra; Shaw and Kamen, *Cell,* 46:659–667, 1986).

EXAMPLE 4

IκB-β INTERACTS WITH p65 AND c-REL

Figure 3C:
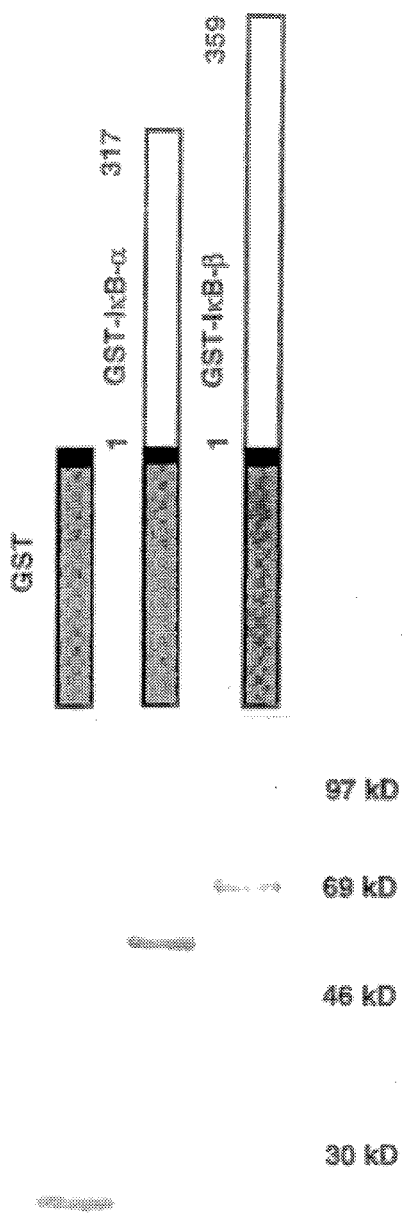
Figure 3D:
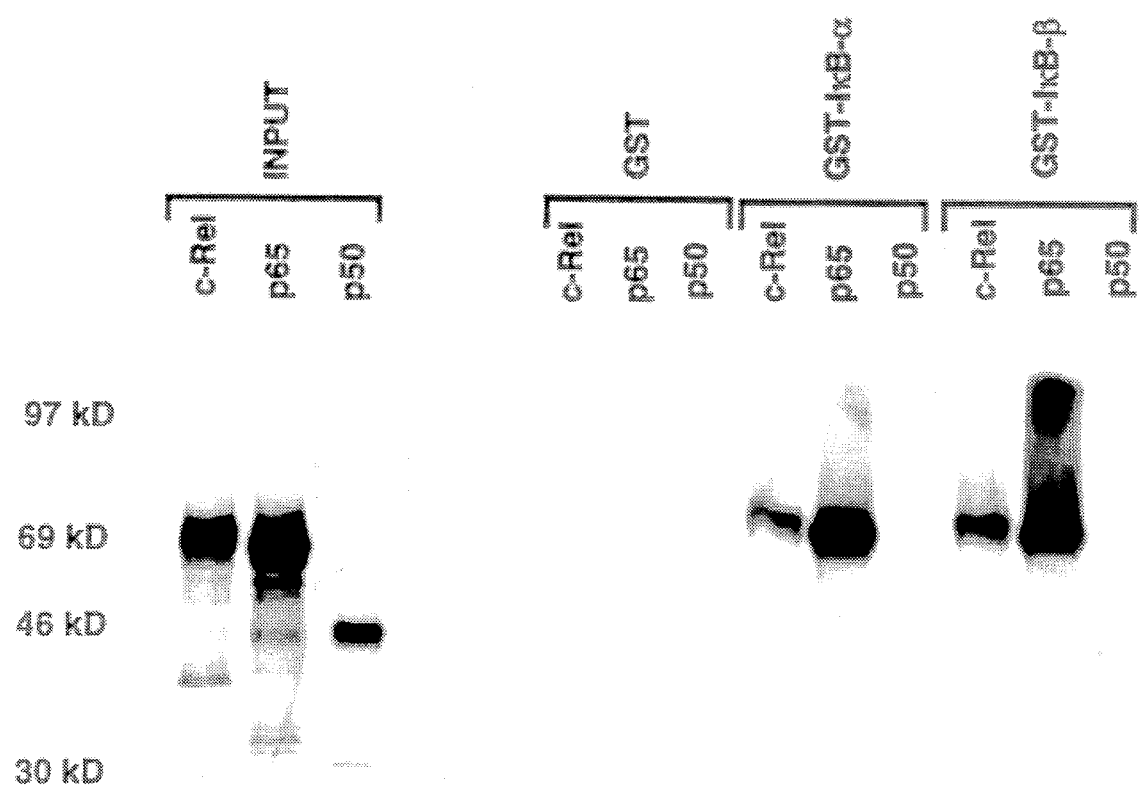

To being characterizing the properties of the protein encoded by the cDNA, the clone was translated in vitro in rabbit reticulocyte lysate. FIGS. 3A–3D show activity of IκB-β in vitro and expressed in vivo. In FIG. 3A, the cDNAs encoding the two IκBs were cloned in a pCDNA 3 vector under the control of a T7 promoter and were used to program TNT rabbit reticulocyte coupled transcription-translation systems. The translated proteins were run on SDS-PAGE and visualized by fluorography. FIG. 3B shows reticulocyte lysates which contain an endogenous NF-κB that is primarily a p50:p 65 heterodimer. Addition of purified rabbit p50:p65 NF-κB increases the signal, facilitating the subsequent assay for IκB activity. The TNT lysates were supplemented with purified rabbit NF-κB for the assays as indicated by '+NF-κB'. To generate the antisense RNA's, the plasmids were linearized with Bam H1 which cuts at the 5' end and instead of T7 RNA polymerase and SP6 RNA polymerase was used. The two 'sense, β' lanes represent two translations programmed with 1 and 2 μg of plasmid respectively. The translation lysates were analyzed on a standard EMSA using an IgκB probe. In FIG. 3C the GST-I κB fusion proteins were purified on a glutathione-agarose affinity column, and the purified proteins were analyzed on SDS-PAGE using coomassie blue staining. FIG. 3D shows the specificity of GST-IκB proteins for p50, p65 and c-Rel. GST-IκB fusion proteins were partially purified by FPLC Mono Q and gel-filtration chromatography. 50 ng of each of the partially purified GST-fusion proteins were mixed with 6 μl of the $^{35}$S-labeled, in vitro translated p50, p65 and c-Rel. After incubating at room temperature for 5 mins, 20 μl of a 1:1 slurry of glutathione-agarose was added, incubated for 2 minutes and centrifuged. The agarose beads were washed with PBS and then boiled for 5 minutes in SDS-sample buffer and the eluted proteins were analyzed on a SDS-PAGE. The gel was fixed, treated with Amplify (Amersham), and fluorographed. The input lanes contained 2.5μl of lysate, whereas the GST-lanes represent precipitated proteins from 5 μl of lysate.

Although the open reading frame predicts a protein of 41 kDa, the in vitro translated protein migrated with an apparent Mr of 45 kD which is very similar to the size of the purified protein (FIG. 3A). The small amount of the 45 kD protein synthesized could efficiently inhibit the DNA binding of endogenous NF-κB in rabbit reticulocyte lysates (which is primarily p50:p65) (FIG. 3B) (Davis, et al., supra). The translated IκB-β could also inhibit DNA binding of exogenous NF-κB (p50:p65 purified from rabbit lungs) when added to the lysates. However, the low amount of in vivo translated IκB-β protein that was synthesized was not sufficient for carrying out a systematic, quantitative analysis to determine if IκB-β demonstrated any preference that was distinct from IκB-αfor specific Rel proteins.

To obtain an independent confirmation of the relative affinities of IκB-α and IκB-β for p65 and c-Rel, full length IκB proteins fused to glutathione S-transferase (GST), were produced in bacteria and tested for their ability to bind Rel proteins. The GST-IκB proteins were mixed with in vitro translated, $^{35}$S-labeled Rel proteins (FIG. 3C). The IκB-Rel protein complexes were precipitated with glutathione-agarose, washed extensively and the bound Rel-proteins analyzed by SDS-PAGE followed by fluorography. Both IκB-α and IκB-β efficiently and specifically interacted with and precipitated p65 and c-Rel, but not p50 (FIG. 3D). In both instances, p65 was more efficiently precipitated than c-Rel.

Figure 4A:
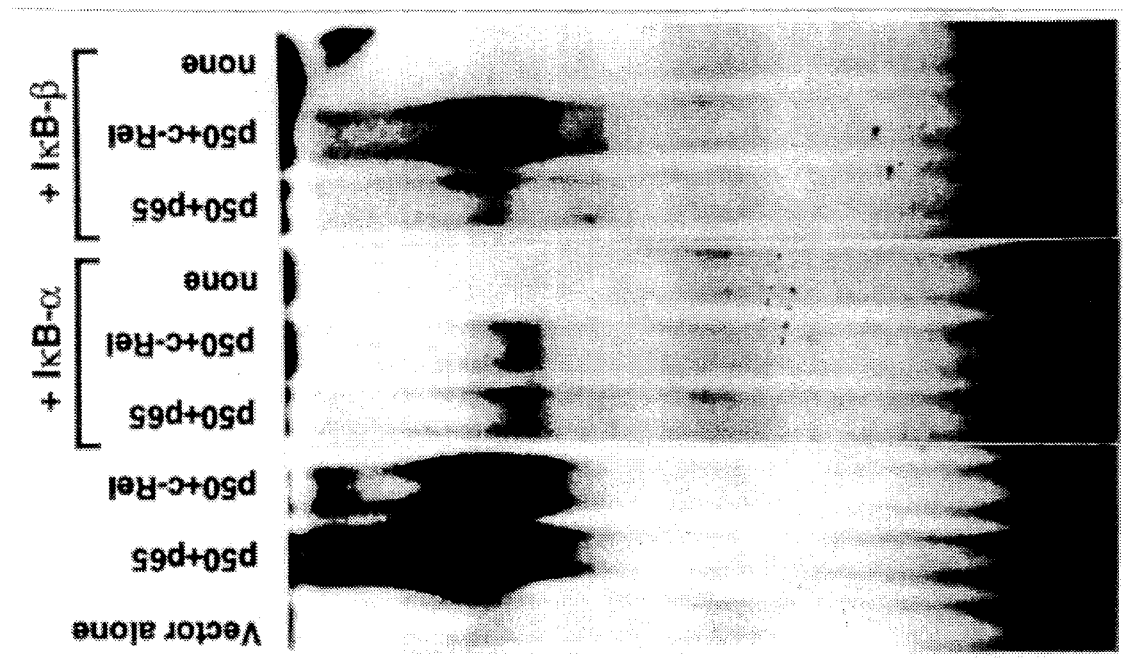

To determine if the cloned cDNA was active in cells, the IκB-α and IκB-β cDNAs were co-transfected into COS cells with p50, p65 and c-Rel cDNAs. FIGS. 4A–4B show inhibition of DNA binding and transcriptional activation in vivo by IκB-β. FIG. 4 A shows inhibition of DNA binding by transfected p50:p65 and p50:c-Rel in COS cells upon cotransfection with IκB-α and IκB-β. COS cells were transfected with the pCDNA 3 vector alone, p50+p65 (3 μg each), p50+c-Rel (3 μg each), p50+c-Rel (3 μg each), p50+p65+ IκB-α or IκB-β (3 μg+3 μg+5 μg) and p50+c-Rel+IκB-α or IκB-β (3 μg+3 μg+5 μg). In all cases the total amount of DNA transfected was equalized to 11 μg by adding vector DNA. The residual complex in the IκB containing lanes included the p50 homodimer complex which is not inhibited by these two IκBs. FIG. 4B shows inhibition of transcription as measured by inclusion of a luciferase reporter construct in transfections, similar to 4A. The amount of transcription as measured by luciferase units from both p65 and c-Rel has been adjusted to a relative 100 units, although c-Rel is actually less efficient in transactivation than p65.

Analysis of the extracts made from the transfected cells indicated that DNA binding by both p65 and c-Rel were inhibited by the IκB isoforms, although it appeared that IκB-β was less effective on c-Rel (FIG. 4A). Inclusion of a reporter construct which contains a luciferase gene driven by two κB sits, in these transfections indicated that both IκB isoforms could inhibit p65 and c-Rel mediated transcription, consistent with the results of the gel retardation assays (FIG. 4B).

EXAMPLE 5

IκB-β mRNA IS WIDELY EXPRESSED IN DIFFERENT TISSUES

Figure 5:
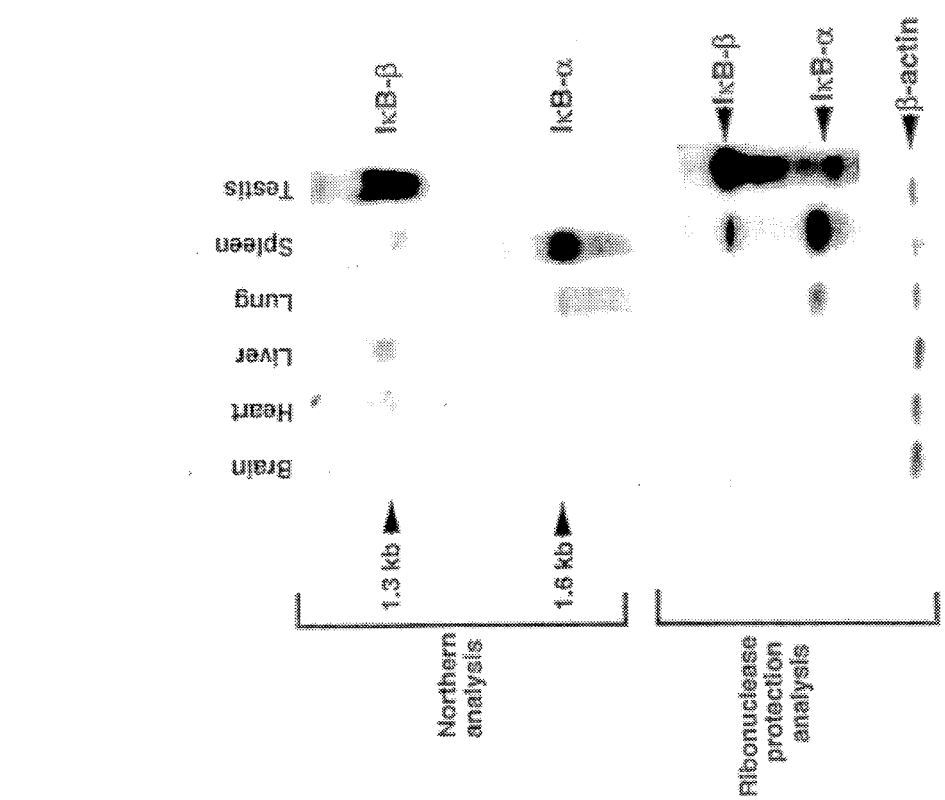
FIG. 5 shows Northern blot and ribonuclease protection analysis for distribution of IκB-α and IκB-β in different mouse tissues. The Northern blot was sequentially probed with cDNAs for IκB-α and IκB-β. The probes for IκB-α and IκB-β in the ribonuclease protection assay were used for hybridization in the same RNA samples. Separate reactions with identical samples were used for β-actin.

To determine whether IκB-β plays a unique function in certain tissues, the pattern of expression of mRNAs for the two IκB isoforms was analyzed using Northern blots. Total RNA from mouse brain, heart, liver, lung, spleen and testis was blotted onto nitrocellulose and probed with the cDNA for IκB-β. FIG. 5 shows expression patterns of IκB-β mRNA. Northern blot and ribonuclease protection analysis for distribution of IκB-α and IκB-β in different mouse tissues. Total RNA (25 μg for Northern blot and 10 μg for ribonuclease protection) from each tissue (Clontech) was used for lane. The Northern blot was sequentially probed with cDNAs for IκBα and IκBβ. The probes for IκB-α and IκB-β in the ribonuclease protection assay were used for hybridization in the same RNA samples. Separate reactions with identical samples were used for β-actin.

The 1.3 kb mRNA encoding IκB-β was detected in low but varying levels in all of the tissues examined with a significantly higher level of expression in testis (FIG. 5). Reprobing of the same blot for IκB-α mRNA revealed that the approximately 1.6 kb IκB-α mRNA was also expressed in different tissues, with the exception that there was no expression in testis and increased expression in spleen. The increased expression of IκB-β in testis may indicate a distinct role for this IκB in testis differentiation or function. The pattern of expression observed was also further verified by carrying out ribonuclease protection assays, using probes for IκB-α and IκB-β in the same RNA samples and the results were identical to those obtained from Northern analysis (FIG. 5).

EXAMPLE 6

IκB-β EXISTS IN VIVO AS A COMPLEX WITH p65 AND c-REL

Figure 6A:
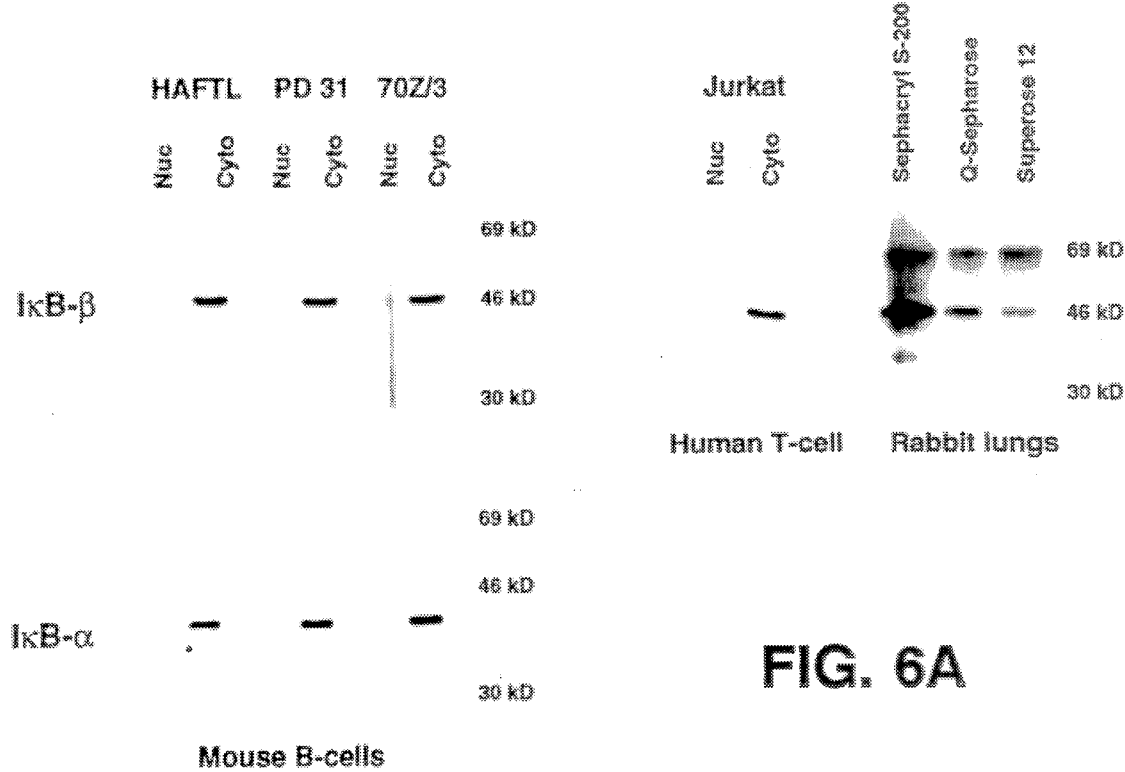
Figure 6B:
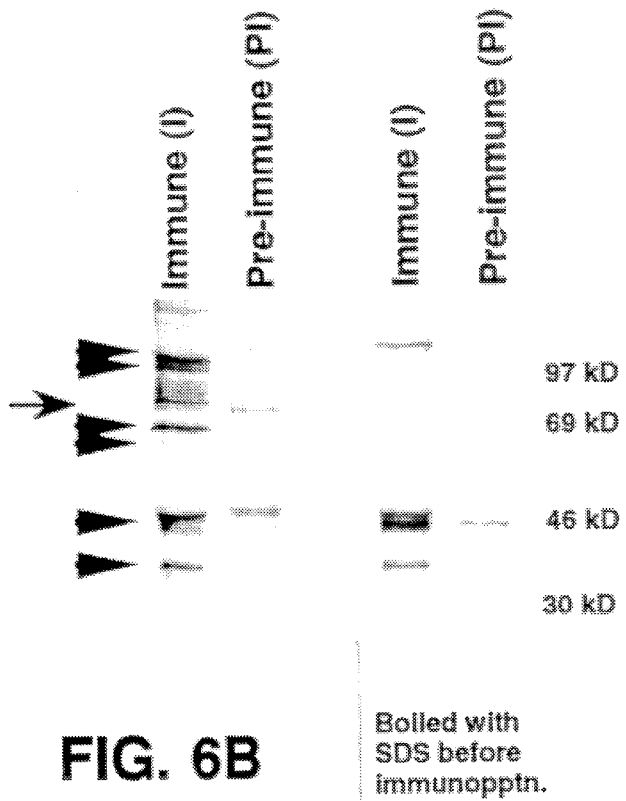

To examine the regulation of IκB-β in greater detail, rabbit polyclonal antisera was raised against the GST-IκB-β fusion protein. FIGS. 6A–6C show immunoblot and immunoprecipitation analysis of IκB-β. In FIG. 6A, cytoplasmic and nuclear extracts were made from different cell lines using a modified NP-40 lysis protocol, 25 μg of each extract was used for Western analysis. The different fractions from rabbit lung are progressively purer chromatography fractions. The Superose 12 fraction is equivalent to the sample used for sequencing. The immunoblot with the mouse B-cell fractions was first used to examine IκB-β and then stripped and reprobed-with an affinity purified IκB-β antibody. In FIG. 6B, immunoprecipitations were carried out on 2×10$^7$ metabolically labeled Jurkat cells using the antiserum to IκB-β and the corresponding pre-immune serum. The bands that appear only with the immune serum are indicated. Immunoprecipitations from boiled samples neutralized with NP-40 were carried out similarly to the other samples. In FIG. 6C, immunoprecipitations were carried out as in FIG. 6B on 1×10$^8$ unlabeled cells with proportionaley greater amounts of immune and pre-immune serum. The immunoprecipitates were then fractionated on SDS-PAGE, electrophoretically transferred to PVDF membranes and immunoblotted with rabbit polyclonal antibodies to p65, c-Rel, IκB-α and IκB-β.

This antiserum recognized one predominant band of approximately 45 kD on immunoblots of both cytosolic extracts from different cells and purified fractions from rabbit lung (FIG. 6A). The size of the protein detected was identical to the size of the purified IκB-β protein. In most cells the majority of IκB-β protein was in the cytoplasm (FIG. 6A). The small amount in the nucleus might be an artifact of the extraction procedure, although the IκB-α protein in these same cells was exclusively cytosolic. An unexpected finding from these experiments was that the level of IκB-β protein in cells appeared to be at least equal, if not greater than IκB-α (using antibodies of equivalent affinity; determined by titrating the antibodies against known amounts of purified, recombinant bacterial proteins) and the lower estimates of its abundance reported previously may have been due to greater losses during purification. The greater amount of IκB-β in cells would suggest that both IκB-α and IκB-β play major roles in regulating the activity NF-κB.

The IκB-β protein was purified as a complex with p50:p65 from human placenta and rabbit lungs, and therefore it was likely that it would exist in cells as a complex with p50:p65 (Davis, et al., supra; Ghosh and Baltimore, supra; Link, et al., supra; Zabel and Baeuerle, *Cell* 61:255–265, 1990). These experiments described above indicated that it was able to bind equally well with both p65 and c-Rel. Therefore in lymphoid cells, which contain both p65 and c-Rel, IκB-β should be in complexes with both Rel-proteins. To test this hypothesis, immunoprecipitations were carried out on Jurkat cell extracts using the IκB-β antiserum and its corresponding pre-immune serum. The immune serum co-precipitated polypeptides of approximately of 40, 46, 65, 70, 105 and 110 kD that resembled the sizes of IκB-α, IκB-β, p65, c-Rel, NF-κB p100 and NF-κB p105, respectively (FIG. 6B) (an additional polypeptide of approximately 80 kD does not correspond to any known Rel protein). Because IκB-β does not label efficiently and overlaps with p50 and immunoglobulin heavy chain, it was not clearly resolved in these gels. A similar pattern was observed upon immunoprecipitating IκB-α from Jurkat cells and WEHI 231 cells (Rice and Ernst, *EMBO J.*, 12:4685–4695, 1993). Immunoprecipitations carried out on extracts that were boiled previously with SDS and neutralized with NP-40 contained only p40 and IκB-β, but not the other proteins indicating that they were non-covalently associated with IκB-β cell extracts (FIG. 6B) (the p40 probably cross-reacted with the antiserum). To provide that these associating polypeptides were indeed members of the Rel family, immunoprecipitations were carried out on unlabeled cell extracts, fractionated on SDS-polyacrylamide gels and immunoblots performed using antibodies to p65, c-Rel, IκB-β and IκB-α (FIG. 6C). Such experiments are hampered by the detection of the primary antibody in the immunoprecipitates by the secondary antibody and therefore bands that overlap with the immunoglobulin bands (−25, 50, 100 and 150 kD) cannot be analyzed. Hence we were unable to determine if p50, p52, p100 and p105 were co-immunoprecipitated with IκB-β using these immunoblots. We were however able to determine that the IκB-β antiserum co-immunoprocipitated the p65 and c-Rel proteins, and that the p40 protein was not IκB-α (FIG. 6C). Also, testing the same immunoblots with the IκB-β antiserum revealed that IκB-β was itself immunoprecipitated. Repeating the same experiment with extracts that had been boiled with SDS prior to immunoprecipitation indicated that only IκB-β was immunoprecipitated. Therefore these results show that besides p50 and p52 (whose presence or absence could not be determined) IκB-β exists in cells as a complex with p65, c-Rel and three other proteins of 80, 105 and 110 kD.

EXAMPLE 7

INDUCTION OF NF-κB ACTIVITY DOES NOT LEAD TO AN UPREGULATION OF IκB-β mRNA LEVELS

The levels of IκB-α and IκB-β mRNA were examined in cell lines representing different stages of mouse B-cell development, particularly because mature B-cells are among the few cell types where NF-κB is constitutively active Sen and Baltimore, *Cell*, 47:921–928, 1986). FIGS. 7A–7B show IκB-β mRNA levels are not regulated by NF-κB. FIG. 7A shows expression of IκB-β and IκB-α in mouse B-cell lines, HAFTL (pro B), PD 31 (pre B), WEHI 231 (early mature B) and S 194 (plasma). Total RNA, 10 μg, made from the different cell lines were used for analysis using ribonuclease protection assay using antisense probes for IκB-α, IκB-β and β-actin. The actin probe was labeled at lower specific activity to allow exposure on the same gel. FIG. 7B shows PD31 pre B cells were stimulated with 2 μg/ml LPS for 4 hours and 12 hours, and 25 ng/ml PMA for 8 hours. The cells were then harvested, and total RNA was made using a guanidium thiocyanate-acid phenol extraction procedure. 20 μg of RNA was analyzed in each lane and the same blot was probed sequentially with IκB-β, β-actin and IκB-α.

Expression of IκB-α mRNA is greatly increased in mature B-cells, because of the nuclear NF-κB in these cells upregulates the expression of the gene in an autoregulatory fashion, probably through NF-κB sites present in the IκB-α promoter (FIG. 7A) (de Martin, et al., *EMBO J.*, 12:2773–2779, 1993; Le Bail, et al., *EMBO J.*, 12:5043–5049, 1993). By contrast, the level of IκB-β mRNA was not significantly altered in mature B-cells, suggesting that its expression was not subjected to upregulation by nuclear NF-κB (FIG. 7A). To prove that the expression of IκB-β mRNA was indeed independent of nuclear NF-κB, pre B cells were treated with PMA and LPS and the levels of IκB-α and IκB-β mRNAs were determined by Northern analysis. After 4 and 12 hours of induction by LPS, there was a significant increase in the level of IκB-α mRNA while the level of IκB-β mRNA remained relatively unaltered (FIG. 7B). Since the 3' untranslated region of the IκB-β mRNA does not contain any AUUUA sequences, which signal rapid RNA turnover and are found in transcripts encoding IκB-α, it is likely that IκB-β mRNA has a long half like (Caput, et al., supra; Haskill, et al., supra; Shaw and Kamen, supra). Therefore, these results suggest that unlike IκB-α, IκB-β may not be utilized for regulating rapid responses but for responding to persistent signals that yield a more permanent change.

EXAMPLE 8

EFFECT OF LPS, IL-1, PMA AND TNF-α ON IκB-α AND IκB-β

Figure 8A:
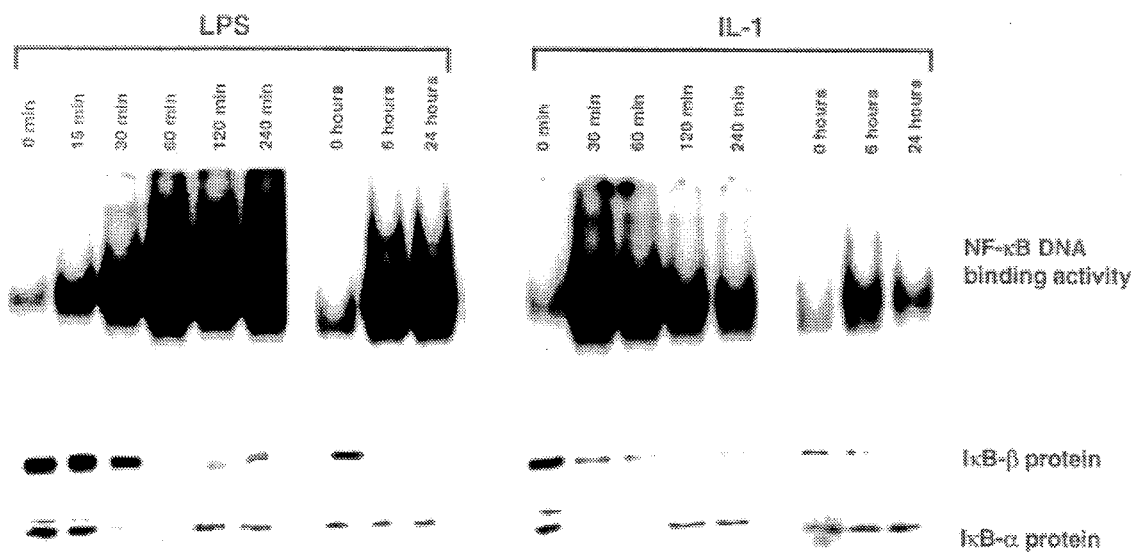
FIGS. 8A–8C, FIG. 8A shows 70Z/3 cells stimulated with either 10 μg/ml or LPS or 0.05 units/ml of IL-1 for the indicated periods of time. The band seen on immunoblots with IκB-β antiserum after 120 and 240 minutes of LPS stimulation is different from the band seen at earlier time points as it migrates slightly faster, however this band also disappears upon further stimulation (6 and 24 hours). Two closely spaced proteins can be distinguished in the IκB-β immunoblots of the IL-1 treated samples.
Figure 8B:
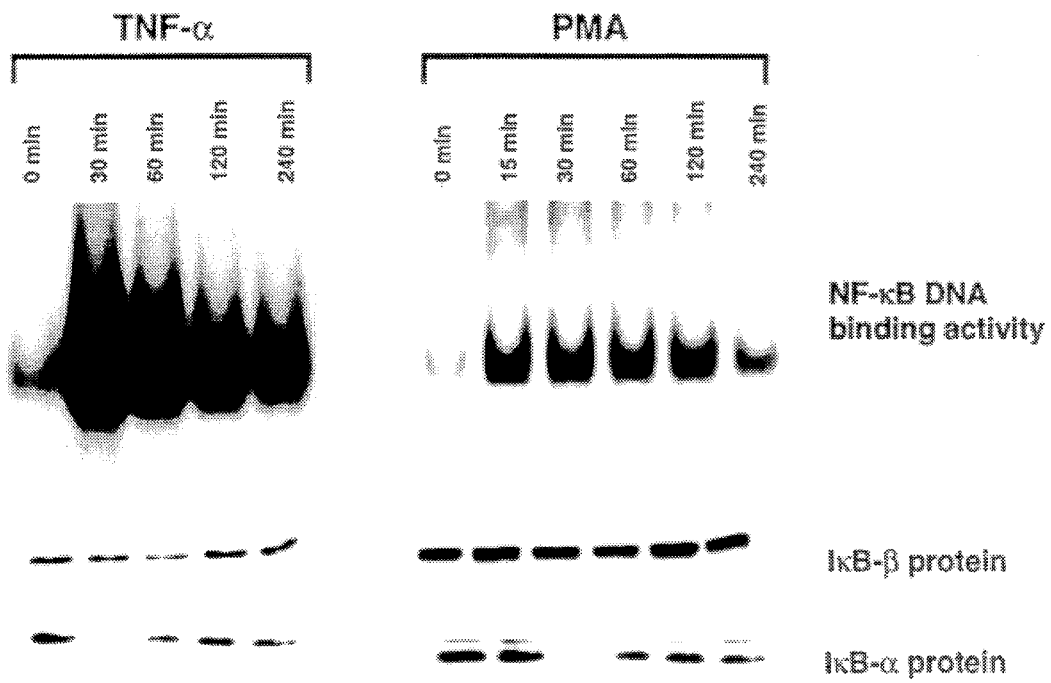
Figure 8C:
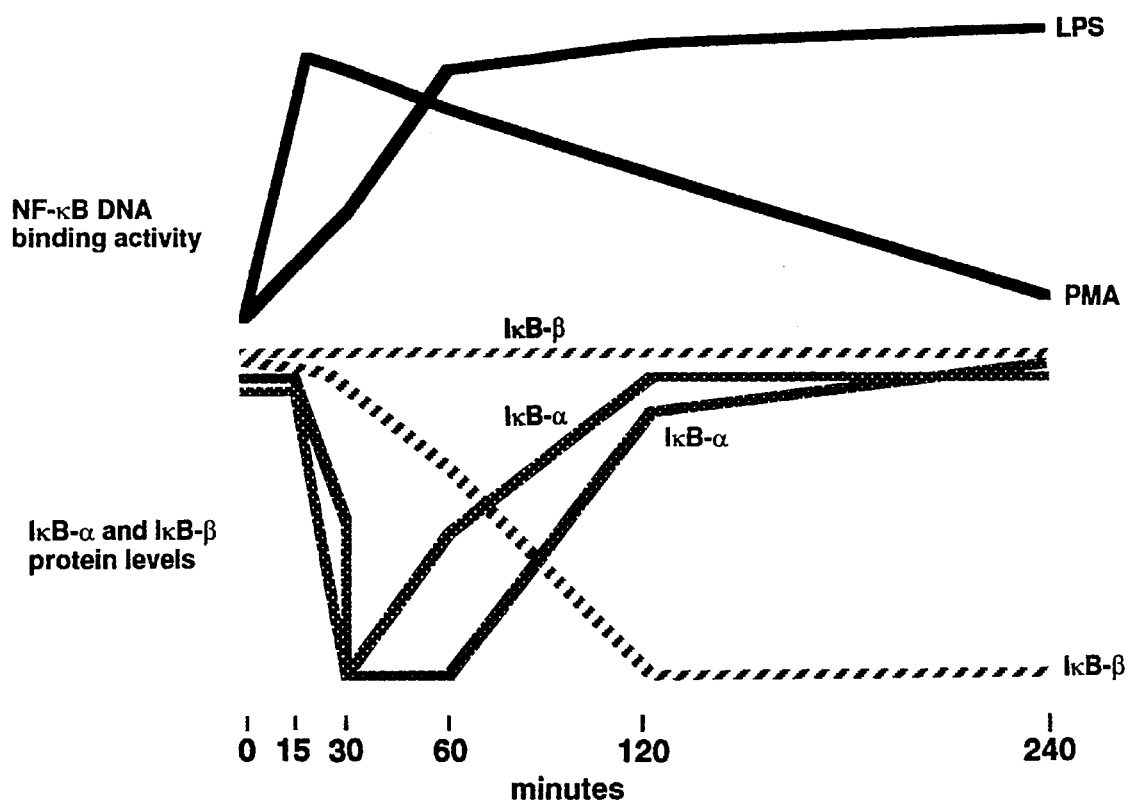

To examine the fate of IκB-β upon activation of NF-κB, pre-B cells were treated with LPS or IL-1 and subcellular fractions were analyzed by immunoblotting and gel retardation assays. FIGS. 8A–8C show LPS, IL-1, PMA and TNF-α cause differential degradation of IκB-α and IκB-β. 70Z/3 cells (for LPS, IL-1 and PMA) and Jurkat cells (for TNF-a) were treated with the different inducers for different lengths of time. 8 µg of the nuclear extract was used for gel retardation assays, while 25 µg of the cytoplasmic extract was used for immunoblotting. In FIG. 8A, 70Z/3 cells were stimulated with either 10 µg/ml of LPS or 0.05 units/ml of IL-1 for the indicated periods of time. The band seen on immunoblots with IκB-β antiserum after 120 and 240 minutes of LPS stimulation is different from the band seen at earlier time points as it migrates slightly faster, however this band also disappears upon further stimulation (6 and 24 hours). Two closely spaced proteins can be distinguished in the IκB-β immunoblots of the IL-1 treated samples. In FIG. 8B, Jurkat cells were stimulated with TNF-a (1 ng/ml) while 70A/3 cells were treated with 25 ng/mil of PMA. FIG. 8C shows a schematic representation of the correlation between degradation of IκB-α and IκB-β with the activation of NF-κβ, in cells treated with LPS or PMA., The curves are for illustrational purposes only and are not quantitative.

Immunoblotting analysis revealed that both inducers led to a loss of IκB-α protein which was rapidly degraded upon stimulation (about 30 minutes) but reappeared within 2 hours (FIG. 8A). By contrast, with both inducers the 45 kDa IκB-β band was less affected at early time points (about 30 minutes), but then its levels decreased and almost disappeared by 2 hours (FIG. 8A). Increasing the period of stimulation of 6 and 24 hours did not alter the overall pattern the level of IκB-α protein was similar to unstimulated controls, while levels of IκB-β was greatly reduced. This experiment highlighted subtle differences in the pattern of IκB-β degradation upon stimulation with LPS and IL-1. Persistent LPS stimulation led to complete loss of IκB-β protein while persistent IL-1 stimulation caused a dramatic decrease in IκB-β levels, although some residual IκB-β could be detected even after 24 hours of stimulation. On immunoblots, the IκB-β antibody occasionally detected a closely spaced doublet of bands in different cells and upon stimulation the upper band was lost preferentially (seen in FIG. 8A). The upper band ban represent a phosphorylated form that is targeted for degradation. Gel retardation assays indicated that nuclear NF-κB DNA binding activity appeared as soon as IκB-α was lost and continued to be detected for the length of the assay (about 24 hours), even though newly synthesized IκB-α accumulated and reappeared within one hour (FIG. 8A). Therefore, the nuclear NF-κB detected at later time points may be released for IκB-β complexes.

Treatment of 70Z/3 cells with PMA or Jurkat cells with TNF-α leads to the rapid but transient induction NF-κB activity. Typically the activity peaks within 30 minutes and gradually decays thereafter, reaching baseline levels within 4 to 6 hours. Therefore, it differs from LPS induction NF-κB, which increases with slower kinetics but then in the continuing presence of the inducer, persists for over 36 hours. Because the persistent induction of NF-κB by LPS was accompanied by the sequential degradation of both IκB-α and IκB-β, we wanted to determine whether the transient induction by PMA or TNF-α affected only the IκB-α complexes. To test this possibility, 70Z/3 cells were treated with PMA and Jurkat cells were treated with TNF-α. Subcellular extracts from these cells were then analyzed by immunoblotting and gel retardation assays. The kinetics of NF-κB activation and decay was similar to previous reports; a peak around 30 minutes followed by significant reduction of the signal by 4 hours (FIG. 8B). The immunoblot of the cytoplasmic fractions indicated that both inducers caused a loss of IκB-α protein by 30 minutes followed by its synthesis and reappearance by 1 hour. However, with both inducers there was no effect on IκB-β, thus implicating degradation of IκB-β in the persistent activation of NF-κB. These results also strongly suggested that the activation of the two IκBs involved distinct signalling pathways. The differential degradation of the two IκB isoforms is schematically depicted in FIG. 8C.

EXAMPLE 9

TPCK AND PDTC BLOCK THE DEGRADATION OF IκB-β

Figure 9:
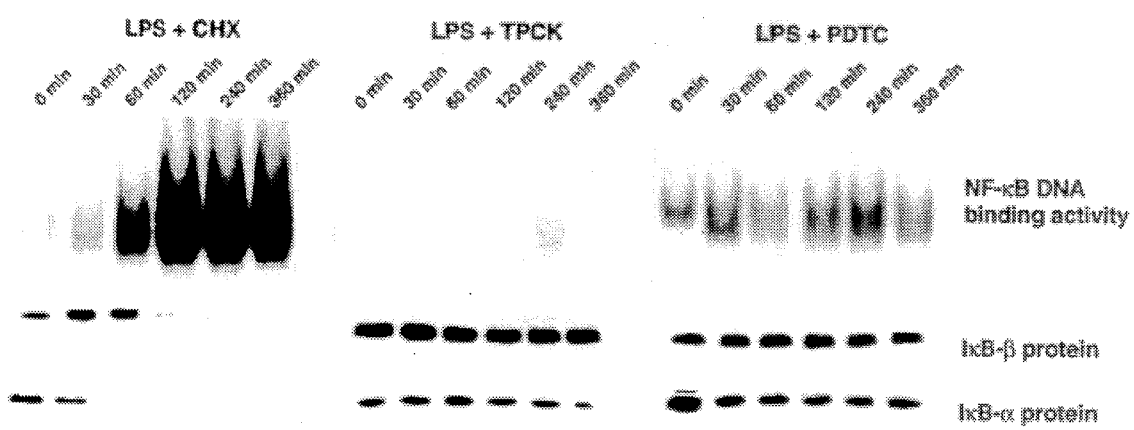
FIG. 9 shows an effect cycloheximide, TPCK and PDTC on turnover or $I_K$β-α and IκB-β. 70Z/3 cells were pre-incubated with 25 μg/ml cycloheximide, 25 μM TPCK or 25 μM PDTC for 30 minutes before stimulating them with 10 μg/ml of LPS for the indicated periods. Nuclear and cytoplasmic extracts were made and analyzed by immunoblotting and gel retardation assays.

To determine whether different signalling pathways targeted to two IκBs, we tested a number of inhibitors was tested and examined for their effect on LPS induced degradation of IκB-α and IκB-β. The degradation of IκB-α upon stimulation of cells is not affected by the protein synthesis inhibitor, cycloheximide, suggesting that no new protein synthesis is required (Henkel, et al., *Nature*, 365:82–85, 1993; Sun, et al., *Science*, 259:1912–1915, 1993). Since activation of IκB-β may occur through a distinct pathway, cycloheximide was examined to determine if it affected IκB-β degradation. 70Z/3 cells were pretested with 25 µg/ml of cycloheximide for 30 minutes, a concentration that blocks all protein synthesis in these cells, and then stimulated them with LPS. Gel retardation assays showed that cycloheximide itself induced some NF-κB activity but did not alter the pattern of NF-κB activation in these cells (FIG. 9). As expected, the IκB-α that disappeared from cycloheximide treated cells did not reappear since no new protein synthesis had taken place. IκB-β also disappeared with a kinetics similar to non-cycloheximide treated cells suggesting that activation of both IκBs occur through distinct signalling pathways that do not require any new protein synthesis.

The chymotrypsin inhibitor TPCK was then tested since it has been demonstrated to block the activation of NF-κB and the accompanying disappearance of IκB-α with all known inducers, leading to the suggestion that it inhibits the protease responsible for IκB-α degradation (Henkel, et al., supra; Mellitis, et al., *Nucl. Acids Res.*, 21:5059–5066, 1993). However, recent studies suggest that TPCK inhibits NF-κB activation by interfering with a common element in the signalling pathways that affect IκB (Palombella, et al., *Cell*, 78:773–785, 1994). To examine the effect of TPCK on IκB-β degradation, 70Z/3 cells were preincubated with TPCK for 30 minutes, followed by LPS treatment for different lengths of time (FIG. 9). Gel retardation assays on the nuclear extracts of induced cells indicated that 25 μM TPCK completely blocked LPS induction of NF-κB.

Immunoblot analysis on the cytoplasmic extracts of the treated cells revealed that neither IκB-α nor IκB-β were affected in the presence of TPCK, a result in keeping with the lack of any induced NF-κB activity. Similar results were seen using PDTC, an anti-oxidant that blocks the activation of NF-κB in response to various inducers through an as yet uncharacterized mechanism involving oxidative free radicals (Schreck, et al., *EMBO J.*, 10:2247–2258, 1991; Sun, et al., supra). In 70Z/3 cells treated with LPS, 25 μM PDTC almost completely blocked both the induction of NF-κB when examined by gel retardation assays and the degradation of IκB-α and IκB-β when examined by immunoblot analysis (FIG. 9). Thus, although the pathways that lead to activation of IκB-α and IκB-β complexes are different, they involve some common steps that are sensitive to TPCK and PDTC.

SUMMARY

The present invention provides the cloning and characterization of a second major isoform of IκB in mammalian cells. In contrast to previous reports, IκB-α and IκB-β were found to display similar inhibitory activities and are present in cells as complexes containing the same proteins (Kerr, et al., *Genes Dev.*, 6:2352–2363, 1992; Kerr, et al., *Genes Dev.*, 5:1464–1476, 1991). The major difference between the two IκB isoforms lies in their responses to different inducers of NF-κB activity. Some inducers elicit a transient activation by affecting only IκB-α complexes while other inducers yield a more permanent change by affecting both IκB-α and IκB-β complexes. Most inducers, including IL-1, TNF-α, PMA or LPS, cause the rapid dissociation of cytoplasmic NF-κB complexes through phosphorylation and subsequent degradation of the IκB-α protein (Beg, et al., supra; Brown, et al., supra; Henkel, et al., *Nature*, 365:82–85, 1993; Mellitis, et al., supra; Palombella, et al., supra; Scott, et al., supra; Sun, et al., supra). The Rel complexes associated with IκB-α are freed and translocate to the nucleus to activate gene expression. The kinetics of the appearance of nuclear NF-κB correlates with the loss of IκB-α, strongly suggesting that the degradation of IκB-α is a prerequisite for releasing the Rel-complexes to which IκB-α was bound. However, the activation of NF-κB also leads to an up-regulation of IκB-α mRNA levels, probably through NF-κB sites in the IκB-α promoter (de Martin, et al., supra; Le Bail, et al., supra). The IκB-α protein subsequently accumulates and soon (~1 hour) reaches the levels in unstimulated cells. Immuno-precipitation of the newly synthesized IκB-α indicates that it is in a complex with NF-κB (Sun, et al., supra). Therefore, the activation of NF-κB occurs transiently because the newly synthesized IκB-α protein blocks persistent activation due to an autoregulatory feed-back loop and if the inducer is present in the environment for a short time, the system is rapidly brought back to the unstimulated state.

While this model explains the transient induction of NF-κB, it failed to explain how nuclear NF-κB can persist for as long as 36 hours when cells are stimulated with LPS, since the IκB-α degradation and resynthesis to original levels takes place within the first 2 hours. The present invention shows that IκB-β begins to be lost after about 1 hour and is absent for as long as LPS is present. This provides a plausible explanation since the long-lived nuclear NF-κB to induce transcription of IκB-β mRNA, unlike IκB-α, suggests that NF-κB released from IκB-β is not down-regulated by an auto-regulatory feed-back mechanism. Therefore, the activation of NF-κB would occur in a novel biphasic fashion in which stimulation with persistent inducers such as LPS, NF-κB would be first released from IκB-α complexes and then from IκB-β complexes.

Although the invention has been described with reference to the presently preferred embodiments, it should be understood that various modifications can be made without departing from the spirit of the invention. Accordingly, the invention is limited only by the following claims.

I claim:

1. An isolated IκB-β polypeptide having the amino acid sequence of SEQ ID NO: 2.

* * * * *

UNITED STATES PATENT AND TRADEMARK OFFICE
CERTIFICATE OF CORRECTION

PATENT NO.   : 5,597,898
DATED        : January 28, 1997
INVENTOR(S)  : Sankar Ghosh It is certified that error appears in the above-identified patent and that said Letters Patent is hereby corrected as shown below:

Column 1, before line 8, insert the following:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Eleventh Day of May, 1999

*Attest:*

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1240 base pairs
        ( B ) TYPE: nucleic acid
        ( C ) STRANDEDNESS: single ( D ) TOPOLOGY: linear ( i i ) MOLECULE TYPE: DNA (genomic)

( v i i ) IMMEDIATE SOURCE:
( B ) CLONE: IkB-beta ( i x ) FEATURE:
( A ) NAME/KEY: CDS
( B ) LOCATION: 74..1150

( x i ) SEQUENCE DESCRIPTION: SEQ ID NO:1:

```
GCGCACTGGA GCTCATCGCA GAGCCCAGCG ACAGGCAGGC GACCACAGGG GGCCACCCGA                    60

GGTGGCTGGG GCC ATG GCC GGG GTC GCG TGC TTG GGG AAA ACT GCG GAT                      109
            Met Ala Gly Val Ala Cys Leu Gly Lys Thr Ala Asp
             1           5                  10

GCC GAT GAA TGG TGC GAC AGC GGC CTG GGC TCT CTA GGT CCC GAC GCA                      157
Ala Asp Glu Trp Cys Asp Ser Gly Leu Gly Ser Leu Gly Pro Asp Ala
         15                  20                  25

GCG GCT CCC GGA GGA CCA GGT CTG GGC GCA GAG CTT GGC CCA GAG CTG                      205
Ala Ala Pro Gly Gly Pro Gly Leu Gly Ala Glu Leu Gly Pro Glu Leu
     30                  35                  40

TCG TGG GCG CCC TTA GTC TTT GGC TAC GTC ACT GAG GAT GGG GAC ACA                      253
Ser Trp Ala Pro Leu Val Phe Gly Tyr Val Thr Glu Asp Gly Asp Thr
 45                  50                  55                  60

GCC CTG CAC TTG GCT GTG ATT CAT CAG CAT GAG CCC TTC CTG GAT TTC                      301
Ala Leu His Leu Ala Val Ile His Gln His Glu Pro Phe Leu Asp Phe
                 65                  70                  75

CTC CTG GGC TTT TCC GCC GGC CAC GAG TAC CTT GAC CTG CAG AAT GAC                      349
Leu Leu Gly Phe Ser Ala Gly His Glu Tyr Leu Asp Leu Gln Asn Asp
             80                  85                  90

CTA GGC CAA ACA GCC CTG CAT CTA GCA GCC ATC CTT GGG GAG GCA TCT                      397
Leu Gly Gln Thr Ala Leu His Leu Ala Ala Ile Leu Gly Glu Ala Ser
         95                 100                 105

ACA GTA GAG AAG TTG TAT GCA GCC GGT GCA GGA GTG TTG GTG GCT GAG                      445
Thr Val Glu Lys Leu Tyr Ala Ala Gly Ala Gly Val Leu Val Ala Glu
     110                 115                 120

AGA GGG GGC CAC ACG GCA TTG CAC TTG GCC TGC CGG GTC AGG GCA CAC                      493
Arg Gly Gly His Thr Ala Leu His Leu Ala Cys Arg Val Arg Ala His
125                 130                 135                 140

ACG TGC GCG TGC GTA CTG CTC CAG CCC CGT CCC AGC CAC CCA AGA GAT                      541
Thr Cys Ala Cys Val Leu Leu Gln Pro Arg Pro Ser His Pro Arg Asp
                145                 150                 155

GCC TCA GAT ACC TAC CTC ACT CAG AGC CAG GAC TGT ACC CCA GAC ACC                      589
Ala Ser Asp Thr Tyr Leu Thr Gln Ser Gln Asp Cys Thr Pro Asp Thr
            160                 165                 170

AGC CAT GCC CCT GCT GCC GTG GAT TCC CAA CCC AAC CCA GAG AAC GAA                      637
Ser His Ala Pro Ala Ala Val Asp Ser Gln Pro Asn Pro Glu Asn Glu
        175                 180                 185

GAG GAG CCG CGT GAT GAA GAC TGG AGG CTA CAA CTA GAA GCT GAA AAC                      685
Glu Glu Pro Arg Asp Glu Asp Trp Arg Leu Gln Leu Glu Ala Glu Asn
    190                 195                 200

TAT GAT GGC CAT ACC CCA CTC CAT GTA GCT GTC ATC CAC AAA GAT GCA                      733
Tyr Asp Gly His Thr Pro Leu His Val Ala Val Ile His Lys Asp Ala
205                 210                 215                 220

GAG ATG GTC CGG CTG CTC AGG GAT GCC GGA GCC GAC CTC AAT AAA CCG                      781
Glu Met Val Arg Leu Leu Arg Asp Ala Gly Ala Asp Leu Asn Lys Pro
                225                 230                 235

GAG CCT ACG TGT GGC CGG ACC CCT CTG CAC CTG GCA GTA GAA GCC CAG                      829
Glu Pro Thr Cys Gly Arg Thr Pro Leu His Leu Ala Val Glu Ala Gln
            240                 245                 250

GCA GCC AGC GTG CTG GAA CTT CTC CTG AAA GCC GGT GCT GAC CCC ACC                      877
```

|  |  |  | Ala | Ala | Ser<br>255 | Val | Leu | Glu | Leu<br>260 | Leu | Leu | Lys | Ala | Gly | Ala<br>265 | Asp | Pro | Thr |  |
|---|---|---|---|---|---|---|---|---|---|---|---|---|---|---|---|---|---|---|---|

```
GCC  CGC  ATG  TAT  GGG  GGC  CGC  ACC  CCG  CTT  GGC  AGT  GCC  CTG  CTC  CGG      925
Ala  Arg  Met  Tyr  Gly  Gly  Arg  Thr  Pro  Leu  Gly  Ser  Ala  Leu  Leu  Arg
     270                 275                 280

CCC  AAC  CCC  ATC  CTT  GCC  CGC  CTC  CTC  CGT  GCA  CAT  GGG  GCC  CCT  GAA      973
Pro  Asn  Pro  Ile  Leu  Ala  Arg  Leu  Leu  Arg  Ala  His  Gly  Ala  Pro  Glu
285                      290                 295                      300

CCT  GAG  GAC  GGA  GGA  GAT  AAG  CTT  AGC  CCT  TGC  AGC  AGC  AGC  GGC  AGC     1021
Pro  Glu  Asp  Gly  Gly  Asp  Lys  Leu  Ser  Pro  Cys  Ser  Ser  Ser  Gly  Ser
                    305                 310                      315

GAC  AGT  GAC  AGT  GAC  AAC  AGA  GAT  GAG  GGC  GAT  GAA  TAT  GAT  GAC  ATC     1069
Asp  Ser  Asp  Ser  Asp  Asn  Arg  Asp  Glu  Gly  Asp  Glu  Tyr  Asp  Asp  Ile
               320                      325                      330

GTG  GCT  CAC  AGT  GGC  AGG  AGC  CTA  AAC  CGA  CAA  CCG  CCT  TCC  CCG  GCA     1117
Val  Ala  His  Ser  Gly  Arg  Ser  Leu  Asn  Arg  Gln  Pro  Pro  Ser  Pro  Ala
          335                      340                      345

TCC  AAA  CCT  CTT  CCT  GAT  GAC  CCC  AAC  CCT  GCC  TGACTTAAGT  GCTAATATTA     1170
Ser  Lys  Pro  Leu  Pro  Asp  Asp  Pro  Asn  Pro  Ala
     350                      355

ATATAATTTC  CAACTTAATA  AAATTGCAGA  CCTGACAACC  AGAAAAAAAA  AAAAAAAAA            1230

AAAAAAAAA                                                                          1240
```

( 2 ) INFORMATION FOR SEQ ID NO:2:

( i ) SEQUENCE CHARACTERISTICS:
        ( A ) LENGTH: 359 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Gly  Val  Ala  Cys  Leu  Gly  Lys  Thr  Ala  Asp  Ala  Asp  Glu  Trp
 1                  5                   10                      15

Cys  Asp  Ser  Gly  Leu  Gly  Ser  Leu  Gly  Pro  Asp  Ala  Ala  Ala  Pro  Gly
               20                  25                      30

Gly  Pro  Gly  Leu  Gly  Ala  Glu  Leu  Gly  Pro  Glu  Leu  Ser  Trp  Ala  Pro
          35                  40                      45

Leu  Val  Phe  Gly  Tyr  Val  Thr  Glu  Asp  Gly  Asp  Thr  Ala  Leu  His  Leu
     50                  55                      60

Ala  Val  Ile  His  Gln  His  Glu  Pro  Phe  Leu  Asp  Phe  Leu  Leu  Gly  Phe
 65                      70                  75                           80

Ser  Ala  Gly  His  Glu  Tyr  Leu  Asp  Leu  Gln  Asn  Asp  Leu  Gly  Gln  Thr
                    85                  90                       95

Ala  Leu  His  Leu  Ala  Ala  Ile  Leu  Gly  Glu  Ala  Ser  Thr  Val  Glu  Lys
               100                 105                 110

Leu  Tyr  Ala  Ala  Gly  Ala  Gly  Val  Leu  Val  Ala  Glu  Arg  Gly  Gly  His
          115                 120                 125

Thr  Ala  Leu  His  Leu  Ala  Cys  Arg  Val  Arg  Ala  His  Thr  Cys  Ala  Cys
     130                 135                 140

Val  Leu  Leu  Gln  Pro  Arg  Pro  Ser  His  Pro  Arg  Asp  Ala  Ser  Asp  Thr
145                 150                 155                      160

Tyr  Leu  Thr  Gln  Ser  Gln  Asp  Cys  Thr  Pro  Asp  Thr  Ser  His  Ala  Pro
               165                 170                 175

Ala  Ala  Val  Asp  Ser  Gln  Pro  Asn  Pro  Glu  Asn  Glu  Glu  Pro  Arg
          180                 185                 190

Asp  Glu  Asp  Trp  Arg  Leu  Gln  Leu  Glu  Ala  Glu  Asn  Tyr  Asp  Gly  His
```

```
            195                      200                      205
Thr  Pro  Leu  His  Val  Ala  Val  Ile  His  Lys  Asp  Ala  Glu  Met  Val  Arg
     210                      215                      220

Leu  Leu  Arg  Asp  Ala  Gly  Ala  Asp  Leu  Asn  Lys  Pro  Glu  Pro  Thr  Cys
225            230                      235                           240

Gly  Arg  Thr  Pro  Leu  His  Leu  Ala  Val  Glu  Ala  Gln  Ala  Ala  Ser  Val
                    245                      250                      255

Leu  Glu  Leu  Leu  Leu  Lys  Ala  Gly  Ala  Asp  Pro  Thr  Ala  Arg  Met  Tyr
               260                      265                      270

Gly  Gly  Arg  Thr  Pro  Leu  Gly  Ser  Ala  Leu  Leu  Arg  Pro  Asn  Pro  Ile
          275                      280                      285

Leu  Ala  Arg  Leu  Leu  Arg  Ala  His  Gly  Ala  Pro  Glu  Pro  Glu  Asp  Gly
     290                      295                      300

Gly  Asp  Lys  Leu  Ser  Pro  Cys  Ser  Ser  Ser  Gly  Ser  Asp  Ser  Asp  Ser
305                      310                      315                      320

Asp  Asn  Arg  Asp  Glu  Gly  Asp  Glu  Tyr  Asp  Asp  Ile  Val  Ala  His  Ser
               325                      330                      335

Gly  Arg  Ser  Leu  Asn  Arg  Gln  Pro  Pro  Ser  Pro  Ala  Ser  Lys  Pro  Leu
               340                      345                      350

Pro  Asp  Asp  Pro  Asn  Pro  Ala
          355
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..12

( x i ) SEQUENCE DESCRIPTION: SEQ ID NO:3:

```
Leu  Tyr  Ala  Ala  Xaa  Ala  Gly  Val  Cys  Val  Ala  Glu
1              5                        10
```

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..18

( x i ) SEQUENCE DESCRIPTION: SEQ ID NO:4:

```
Leu  Gln  Leu  Glu  Ala  Glu  Asn  Tyr  Asp  Gly  Xaa  Thr  Pro  Leu  Xaa  Val
1              5                        10                       15

Ala  Val
```

( 2 ) INFORMATION FOR SEQ ID NO:5:

( i ) SEQUENCE CHARACTERISTICS:
        ( A ) LENGTH: 17 amino acids
        ( B ) TYPE: amino acid ( C ) STRANDEDNESS: single
            ( D ) TOPOLOGY: linear ( i i ) MOLECULE TYPE: peptide ( i x ) FEATURE:
            ( A ) NAME/KEY: Peptide
            ( B ) LOCATION: 1..17

( x i ) SEQUENCE DESCRIPTION: SEQ ID NO:5:

Pro Leu His Leu Ala Val Glu Ala Gln Ala Ala Asp Val Leu Glu Leu
1               5                   1 0                 1 5

Leu